United States Patent
Greiner et al.

(10) Patent No.: US 9,327,134 B2
(45) Date of Patent: *May 3, 2016

(54) IMPLANTABLE ELECTROACUPUNCTURE DEVICE AND METHOD

(71) Applicant: Valencia Technologies Corporation, Valencia, CA (US)

(72) Inventors: Jeffrey H. Greiner, Valencia, CA (US); David K. L. Peterson, Valencia, CA (US); Chuladatta Thenuwara, Castaic, CA (US); Stacy O. Greiner, Valencia, CA (US)

(73) Assignee: Valencia Technologies Corporation, Valencia, CA (US)

( * ) Notice: Subject to any disclaimer, the term of this patent is extended or adjusted under 35 U.S.C. 154(b) by 333 days.

This patent is subject to a terminal disclaimer.

(21) Appl. No.: 13/796,314

(22) Filed: Mar. 12, 2013

(65) Prior Publication Data

US 2014/0214113 A1    Jul. 31, 2014

Related U.S. Application Data

(63) Continuation-in-part of application No. 13/598,582, filed on Aug. 29, 2012, now Pat. No. 8,965,511, and a
(Continued)

(51) Int. Cl.
*A61N 1/00*     (2006.01)
*A61N 1/375*    (2006.01)
(Continued)

(52) U.S. Cl.
CPC .......... *A61N 1/3756* (2013.01); *A61N 1/36114* (2013.01); *A61N 1/36175* (2013.01);
(Continued)

(58) Field of Classification Search
CPC .......... A61N 1/36125; A61N 1/36175; A61N 1/37205; A61N 1/3756; A61N 1/375; A61N 1/3758; A61N 1/3782; A61N 1/3787; A61H 39/002; A61B 5/00
See application file for complete search history.

(56) References Cited

U.S. PATENT DOCUMENTS 4,031,899 A    6/1977   Renirie
4,157,720 A    6/1979   Greatbatch
(Continued)

FOREIGN PATENT DOCUMENTS

EP    1145736 A2    10/2001
WO    WO 01/41869 A1    6/2001
(Continued)

OTHER PUBLICATIONS

Luo HC, Jia YK & Li Z. 'Electro-acupuncture vs. amitriptyline in the treatment of depressive states.' Journal of Traditional Chinese Medicine 1985; 5:3-8.
(Continued)

*Primary Examiner* — Christopher D Koharski
*Assistant Examiner* — Elizabeth K So
(74) *Attorney, Agent, or Firm* — Bryant R. Gold

(57) ABSTRACT

An implantable electroacupuncture device (IEAD) treats a medical condition of a patient through application of electroacupuncture (EA) stimulation pulses applied at a target tissue location, such as an acupoint. The IEAD comprises an implantable, coin-sized, self-contained, leadless electroacupuncture device having at least two electrodes attached to an outside surface of its housing. The device generates EA stimulation pulses in accordance with a specified stimulation regimen. Power management circuitry within the device allows a primary battery, having a high internal impedance, to be used to power the device. The stimulation regimen generates stimulation pulses during a stimulation session of duration T3 minutes applied every T4 minutes. The duty cycle, or ratio T3/T4, is very low, no greater than 0.05. The low duty cycle and careful power management allow the IEAD to perform its intended function for several years.

20 Claims, 25 Drawing Sheets

Related U.S. Application Data continuation-in-part of application No. 13/622,653, filed on Sep. 19, 2012, now Pat. No. 8,996,125, and a continuation-in-part of application No. 13/630,522, filed on Sep. 28, 2012, now Pat. No. 9,173,811.

(60) Provisional application No. 61/609,875, filed on Mar. 12, 2012, provisional application No. 61/672,257, filed on Jul. 16, 2012, provisional application No. 61/672,661, filed on Jul. 17, 2012, provisional application No. 61/673,254, filed on Jul. 19, 2012, provisional application No. 61/674,691, filed on Jul. 23, 2012, provisional application No. 61/676,275, filed on Jul. 26, 2012.

(51) Int. Cl.
  *A61N 1/36* (2006.01)
  *A61N 1/372* (2006.01)
  *A61N 1/378* (2006.01)

(52) U.S. Cl.
  CPC ......... *A61N1/37205* (2013.01); *A61N 1/36117* (2013.01); *A61N 1/36125* (2013.01); *A61N 1/3758* (2013.01); *A61N 1/3782* (2013.01); *H01L 2224/48091* (2013.01); *Y10T 29/49002* (2015.01)

(56) References Cited

U.S. PATENT DOCUMENTS

| | | |
|---|---|---|
| 4,345,604 A | 8/1982 | Renirie |
| 4,528,072 A | 7/1985 | Kurosawa |
| 4,535,784 A | 8/1985 | Rohlicek |
| 4,566,064 A | 1/1986 | Whitaker |
| 5,195,517 A | 3/1993 | Chen |
| 5,199,248 A | 4/1993 | Hale |
| 5,199,428 A | 4/1993 | Obel |
| 5,211,175 A | 5/1993 | Gleason |
| 5,250,068 A | 10/1993 | Ideguchi |
| 5,251,637 A | 10/1993 | Shalvi |
| 5,372,605 A | 12/1994 | Adams |
| 5,544,656 A | 8/1996 | Pitsillides |
| 5,609,617 A | 3/1997 | Shealy |
| 5,707,400 A | 1/1998 | Terry, Jr. |
| 5,891,181 A | 4/1999 | Zhu |
| 6,006,134 A | 12/1999 | Hill |
| 6,178,352 B1 | 1/2001 | Gruzdowich |
| 6,393,324 B2 | 5/2002 | Gruzdowich et al. |
| 6,522,926 B1 | 2/2003 | Kieval |
| 6,658,298 B2 | 12/2003 | Gruzdowich |
| 6,735,475 B1 | 5/2004 | Whitehurst |
| 6,839,596 B2 | 1/2005 | Nelson |
| 6,950,707 B2 | 9/2005 | Whitehurst |
| 6,978,174 B2 | 12/2005 | Gelfand |
| 7,003,352 B1 | 2/2006 | Whitehurst |
| 7,013,177 B1 | 3/2006 | Whitehurst |
| 7,046,499 B1 | 5/2006 | Imani |
| 7,136,701 B2 | 11/2006 | Greatbatch |
| 7,155,279 B2 | 12/2006 | Whitehurst |
| 7,162,303 B2 | 1/2007 | Levin |
| 7,171,266 B2 | 1/2007 | Gruzdowich |
| 7,203,548 B2 | 4/2007 | Whitehurst |
| 7,292,890 B2 | 11/2007 | Whitehurst |
| 7,321,792 B1 | 1/2008 | Min et al. |
| 7,373,204 B2 | 5/2008 | Gelfand |
| 7,440,806 B1 | 10/2008 | Whitehurst |
| 7,444,180 B2 | 10/2008 | Kuzma |
| 7,610,100 B2 | 10/2009 | Jaax |
| 7,620,451 B2 | 11/2009 | Demarais |
| 7,657,316 B2 | 2/2010 | Jaax |
| 7,962,219 B2 | 6/2011 | Jaax |
| 2002/0016568 A1 | 2/2002 | Lebel |
| 2003/0078642 A1 | 4/2003 | Malaney |
| 2003/0158588 A1 | 8/2003 | Rizzo |
| 2003/0171790 A1 | 9/2003 | Nelson |
| 2003/0187485 A1 | 10/2003 | Sturman |
| 2003/0195583 A1 | 10/2003 | Gruzdowich |
| 2003/0195585 A1 | 10/2003 | Gruzdowich |
| 2003/0220668 A1 | 11/2003 | Shealy |
| 2003/0236558 A1 | 12/2003 | Whitehurst |
| 2005/0107832 A1 | 5/2005 | Bernabei |
| 2005/0228460 A1 | 10/2005 | Levin |
| 2005/0234533 A1 | 10/2005 | Schulman |
| 2006/0041283 A1 | 2/2006 | Gelfand |
| 2006/0184209 A1 | 8/2006 | John |
| 2007/0005119 A1 | 1/2007 | Crohn |
| 2007/0219595 A1 | 9/2007 | He |
| 2007/0255319 A1 | 11/2007 | Greenberg |
| 2007/0265680 A1 | 11/2007 | Liu |
| 2008/0015572 A1 | 1/2008 | Johnson |
| 2008/0091255 A1 | 4/2008 | Caparso |
| 2008/0097529 A1 | 4/2008 | Parramon |
| 2009/0192555 A1 | 7/2009 | Schleicher |
| 2009/0210026 A1 | 8/2009 | Solberg |
| 2009/0292341 A1 | 11/2009 | Parramon |
| 2010/0042137 A1 | 2/2010 | Oronsky |
| 2010/0069992 A1 | 3/2010 | Aghassian |
| 2010/0211132 A1 | 8/2010 | Nimmagadda |
| 2010/0324624 A1 | 12/2010 | Chang |
| 2010/0327887 A1 | 12/2010 | Denison |
| 2011/0106219 A1 | 5/2011 | Cauller |
| 2011/0106220 A1 | 5/2011 | DeGiorgio |
| 2011/0112603 A1 | 5/2011 | DeGiorgio |
| 2011/0172739 A1 | 7/2011 | Mann |
| 2011/0218589 A1 | 9/2011 | DeGiorgio |
| 2011/0218590 A1 | 9/2011 | DeGiorgio |
| 2012/0022612 A1 | 1/2012 | Littlewood |
| 2012/0259390 A1 | 10/2012 | Canion |
| 2013/0041396 A1 | 2/2013 | Ryotokuji |
| 2014/0214111 A1 | 7/2014 | Greiner |
| 2014/0214112 A1 | 7/2014 | Greiner |
| 2014/0214114 A1 | 7/2014 | Greiner |
| 2014/0214115 A1 | 7/2014 | Greiner |
| 2014/0214116 A1 | 7/2014 | Peterson |
| 2014/0214117 A1 | 7/2014 | Greiner |
| 2014/0214118 A1 | 7/2014 | Greiner |
| 2014/0214119 A1 | 7/2014 | Greiner |
| 2014/0214124 A1 | 7/2014 | Greiner |
| 2014/0214125 A1 | 7/2014 | Greiner |
| 2014/0214126 A1 | 7/2014 | Greiner |
| 2014/0214127 A1 | 7/2014 | Greiner |
| 2014/0214128 A1 | 7/2014 | Peterson |
| 2014/0214133 A1 | 7/2014 | Thenuwara |
| 2014/0214134 A1 | 7/2014 | Peterson |
| 2014/0214144 A1 | 7/2014 | Peterson |

FOREIGN PATENT DOCUMENTS

| | | |
|---|---|---|
| WO | WO 02/00294 A1 | 1/2002 |
| WO | WO 2014/016511 A2 | 10/2014 |
| WO | WO 2014/159433 A1 | 10/2014 |

OTHER PUBLICATIONS

Luo H, Meng F, Jia Y and Zhao X. 'Clinical research on the therapeutic effect of the electro-acupuncture treatment in patients with depression.' Psychiatry Clin Neurosci 1998; 52 Suppl: S38-S340.

Luo H, Ureil H, & Shen Y. Comparative study of electroacupuncture and fluoxetine for treatment of depression. Chin J. Psychiatry, 2003; 36(4): 215. Chinese with English abstract.

Luo 1985; 'Clinical Research on the therapeutic effect of the elctro-acupuncture treatment in patients with depression.' Psychiatry Clin Neurosci 1998; 52 Suppl: S338-S340.

Han 2006; Han C, Li XW, Luo HC. 'Comparative study of electro-acupuncture and maprotiline in treating depression.' Zhongguo Zhong Xi Yi Jie He Za Zhi. 2002; 22(7): 512-514. Chinese with English Abstract.

Luo H, Shen Y, Meng F, Jia Y, Zhao X, Guo H & Feng X. Preliminary research on treatment of common mental disorders with computer controlled electroacupuncture. Chin J Integr Med 1996; 2(2): 98-100.

(56) References Cited

OTHER PUBLICATIONS

Leo, Salvador, Ligot. 'A systematic review of randomized controlled trials of acupuncture in the treatment of depression.' Journal of Affective Disorders 2006.
Fu WB, Fan L, Zhu XP, He Q, Wang L, Zhuang LX, Liu YS, Tang CZ, Li YW, Meng CR, Zhang HL, Yan J. "Acupuncture for treatment of depressive neurosis: a multi-center randomized controlled study." 2008. Zhongguo Zhen Jiu. Chinese Acupuncture and Moxibustion. 28(1): 3-6. Chinese with English Abstract.
Meng F, Luo H, Shen Y, Shu L, Liu J. Plasma NE concentrations and 24 hours urinary MHPG SO4 excretion changes after electro-acupuncture treatment in endogenous depression. World J. Acup-Mox. 1994; 4: 45-52.
Wang H, Yu E, Zhao J. "Clinical analysis of common psychosis treated by electroacupuncture in 129 cases." Journal of Clinical Acupuncture and Moxbiusion. 1999; (1): 42.
Luo H, Shen Y, Meng F, Jia Y, Zhao X, Guo H Feng X. "Preliminary research on treatment of common mental disorders with computer controlled electroacupuncture." Chin J Integr Med 1996; 2(2): 98-100.
Chen E. Cross-Sectional Anatomy of Acupoints. Churchill Livingstone. 1995. p. 114.
Shrader L, Cook P, Maremont E, DeGiorgio C. "Trigeminal nerve stimulation in major depressive disorder: first proof of concept in an open pilot trial." Epilepsy Behav 2011; 22:475-8.
"Trigeminal Nerve." http://en.wikipedia.org/wiki/trigeminalnerve.
Greiner, U.S. Appl. No. 61/541,061, filed Sep. 29, 2011.
Greiner, U.S. Appl. No. 61/626,339, filed Sep. 23, 2011.
Peterson, U.S. Appl. No. 61/672,661, filed Jul. 17, 2012.
Peterson, U.S. Appl. No. 61/673,254, filed Jul. 19, 2012.
Thenuwara, U.S. Appl. No. 61/676,275, filed Jul. 26, 2012.
Thenuwara, U.S. Appl. No. 13/777,901, filed Feb. 26, 2013.
Peterson, U.S. Appl. No. 13/769,699, filed Feb. 18, 2013.
Greiner, U.S. Appl. No. 61/575,869, filed Aug. 30, 2011.
Peterson, U.S. Appl. No. 61/606,995, filed Mar. 6, 2012.
Peterson, U.S. Appl. No. 61/609,875, filed Mar. 12, 2012.
Peterson, U.S. Appl. No. 13/776,155, filed Feb. 25, 2013.
Peterson, U.S. Appl. No. 61/672,257, filed Jul. 16, 2012.
Peterson, U.S. Appl. No. 61/674,691, filed Jul. 23, 2012.
Greiner, U.S. Appl. No. 13/598,582, filed Aug. 29, 2012.
Greiner, U.S. Appl. No. 13/622,653, filed Sep. 19, 2012.
Greiner, U.S. Appl. No. 13/630,522, filed Sep. 28, 2012.
Song, Kiseok, "The Compact Electro-Acupuncture System for Multi-Modal Feedback Electro-Acupuncture Treatment," 34th Annual International Conference of the IEEE EMBS, San Diego, CA, USA, Aug. 28-Sep. 1, 2012.
Cheung. The Mechanism of Acupuncture Therapy and Clinical Case Studies. Taylor and Francis, published in London. 2001. ISBN 0-415-27254-8. The Forward, Chapters 1-3, 5, 7, 8, 12 and 13.
"Delta-sigma modulation." http://en.wikipedia.org/wiki/Delta_sigma_modulation.
"Acupuncture Today: Electroacupuncture". Feb. 1, 2004. (Retrieved on-line Aug. 9, 2006 at http://www.acupuncturetoday.com/abc/electroacupuncture.php.).
WHO Standard Acupuncture Point Locations in the Western Pacific Region, published by the World Health Organization (WHO), Western Pacific Region, 2008 (updated and reprinted 2009), ISBN 978 92 9061 248 7. The Table of Contents, Forward (p. v-vi), and General Guidelines for Acupuncture Point Locations (pp. 1-21), as well as pp. 25, 26, 29, 33, 35, 39, 45, 64, 66, 71-72, 74, 81, 84-85, 99, 106, 111, 125, 138, 151, 154-155, 188, 197,199, 203, 205 and 213.
"Acupuncture." http://en.wikipedia.org/wiki/Acupuncture.
"Electroacupuncture." http://en.wikipedia.org/wiki/Electroacupuncture.
Li. "Neural Mechanism of Electroacupuncture's Hypotensive Effects", Autonomic Neuroscience: Basic and Clinical 157 (2010) 24-30.
J.C. Longhurst "Central & Peripheral Neural Mechanisms of Acupuncture in Myocardial Ischemia", International Congress Series 1238 (2002) 79-87.
C. Mannheimer et al., "The Problem of Chronic Refractory Angina," European Heart Journal (2002) 23, 355-370.
J. E. Sanderson, "Electrical neurostimulators for pain relief in angina," British Heart Journal (1990) 63:141-143.
Zhou WY, Tjen-A-Looi SC, Longhurst JC. "Brain stem mechanisms underlying acupuncture modality-related modulation of cardiovascular responses in rats," J Appl Physiol 2005, 99:851-860.
Zhou W, Fu LW, Tjen-A-Looi SC, et al., "Afferent mechanisms underlying stimulation of modality-related modulation of acupuncture-related cardiovascular responses," J Appl Physiol 2005, 98:872-880.
Gao, J et al., "Acupuncture pretreatment protects heart from injury in rats with myocardial ischemia and reperfusion via inhibition of the B1-adrenoceptor signaling pathway," Life Sciences 80 (2007) 1484-1489.
Li P. et al., "Reversal of Reflex-Induced Myocardial Ischemia by Median Nerve Stimulation: A Feline Model of Electroacupuncture," American Heart Association Circulation 1998, 97: 1186-1194.
Middlekauf HR, Yu JL, Hui K, et al, "Acupuncture inhibits sympathetic activation during mental stress in advanced heart failure patients," J Cardiac Failure: 8:399-406 (2002).
Jacobsson F, Himmelmann A, Bergbrant A et al.: "The effect of transcutaneous electric nerve stimulation in patients with therapy resistant hypertension." J. Hum. Hypertens. 14(12), 795-798 (2000).
Oka, T., Tsuda, Y., Suzuki, S., Aji, R., Kaneya, S., & Fujino, T., "Treatment of angina pectoris with acupuncture—role of Neiguan," Jpn J. Oriental Med. 38: 85-88.
Kurono Y, Egawa M, Yano T & Shimoo K. "The effect of acupuncture on the coronary arteries as evaluated by coronary angiography: a preliminary report," Am J Chin Med 30: 387-396 (2002).
Lin D, Lin Y, Hu J & Ruan X: "Effect of electroacupuncture on Neiguan and Shenmen Points on heart function after coronary artery bypass grafting in coronary heart disease." Modern Journal of Integrated Traditional Chinese and Western Medicine: 18:2241-41. Abstract. (2009).
Li P, Pitsillides KF, Rendig SV et al: "Reversal of reflex-induced myocardial ischemia by median nerve stimulation: a feline model of electroacupuncture," Circulation 97: 1186-94 (1998).
Tjen-A-Looi SC, Li P, Longhurst JC. "Medullary substrate and differential cardiovascular responses during stimulation of specific acupoints," Am J Physiol Regul Integ Comp Physiol 2004, 287:R852-R862.
Liu XQ, Lu SQ, Luo L: "Influence of acupuncture on epicardial monophasic action potential in vivo in dog with myocardial infarction," Tianjin Journal of Traditional Chinese Medicine 22: 480-481 (2005).
Yang L, Yang J, Wang Q, et al.: "Cardioprotective effects of electroacupuncture pretreatment on patients undergoing heart valve replacement surgery: a randomized controlled trial," Ann Thorac Surg 89:781-6 (2010).
Ballegaard S, Jensen G, Petersen F, et al., "Acupuncture in severe, stable angina pectoris: a randomized trial," Acta Med Scand 220: 307-13 (1986).
Richter A, Herlitz J, Hjalmarson A: "Effect of acupuncture in patients with angina pectoris," Eur Heart J: 12:175-8 (1991).
Quirico PE, Pedrali T. Teaching Atlas of Acupuncture, vol. 1: Channels and Points. pp. 180-196.
Wang JD, Kuo T, Yang C: "An alternative method to enhance vagal activities and suppress sympathetic activities in humans," Autonomic Neuroscience: Basic and clinical 100: 90-95. (2002).
Xie, L., Xie, L., Dong, X.: "124 cases of dyssomnia treated with acupuncture at sishencong points," J. Tradit. Chin. Med. 14, 171-173 (1994).
Han Y, Zhang P, Ning M, et al., "Influence of needling with the combination of back-shu and front-mu points in the heart and pericardium meridian on the electrocardiography of patients with coronary heart disease," Chinese Acupuncture and Moxibustion Jun. 1994. Abstract. (1994).
Cai RL, Hu L, Zhou YP, Wu ZJ, Wang KM, Tang XM, Li M, Lu ZH: "Effects of electroacupuncture of "Shenmen" (HT 7) and "Zhizheng" (SI 7) on cardiac function and electrical activities of cardiac sympathetic nerve in acute myocardial ischemia rabbits," Zhen Ci Yan Jiu. 2007; 32(4): 243-6. Abstract (2007).

(56) References Cited

OTHER PUBLICATIONS

Zhou W, Fu LW, Tjen-A-Looi SC, et al.: "Afferent mechanisms underlying afferent stimulation modality-related modulation of acupuncture-related cardiovascular responses," J Appl Physiol 2005;98:872-880 (2005).

Yang YF, Chou CY, Li TC, Jan YM, Tang NY, Hsieh CL.: "Different effects of acupuncture at shenmen (HT7)-Tongli(HT5) and Shenmen-Neiguan (PC6) points on heart rate variability in healthy subjects." J Chin Med. 2009; 20 (3,4): 97-106 (2009).

Li P & Longhurst JC, "Neural Mechanism of Electroacupuncture's Hypotensive Effects," Autonomic Neuroscience: Basic & Clinical 157:24-30 (2010).

Xiao-Min T, Ling Hu, Ke-Ming L.: "Experimental study on electroacupuncture in "Neiguan" (PC6) on congestive heart failure rats model and its effect of AngII, ET, CGRP," Journal of Chengdu University of Traditional Chinese Medicine. Jan. 2007. Abstract. (2007).

Xu FH, Wang JM: "Clinical observation on acupuncture combined with medication for intractable angina pectoris," Zhongguo Zhen Jiu. 25(2): 89-91, Abstract (2005).

Shi X, Wang ZP, Liu KX. "Effect of acupuncture on heart rate variability in coronary heart disease patients," Zhongguo Zhong Xi Yi Jie He Za Zhi 15(9): 536-8. Abstract (1995).

Chiu YJ, Chi A., Reid I.A. et al., "Cardiovascular and endocrine effects of acupuncture in hypotensive patients," Clin. Exp. Hyperten 19(7), 1047-1063 (1997).

Yuanhua W, Guangqu Z, Xingyou L, Lengxing O, Hongmei S, Bangqi W: "Effect of acupuncture at quchi and taichong on ET and ACE in the blood of patients with hypertension and exploration of its efficacy," Chinese Journal of Integrated Chinese and Western Medicine 24: 1080-83 (2004).

Hongxing Z, Tanga F, Yueping L: "Control observation on acupuncture of Quchi (LI 11) and medication in transient action of decreasing blood pressure," Chinese Acupuncture and Moxibustion. 2001: 11. Abstract (2011).

Swartz, KL. The John Hopkins White Papers: Depression and Anxiety. 2011.

Wheeler, Mark"Non-Invasive Therapy Significantly Improves Depression, Researchers Say," ScienceDailiy.com (Sep. 6, 2010). Orig. published by UCLANews.

Lewis, D. "Trigeminal Nerve Stimulation for Depression," www.helpforDpression.com (Sep. 15, 2011).

"Trigeminal Nerve Stimulation Significantly Improves Depression," www.psypost.org, Friday, Sep. 3, 2010.

Liu Q, Yu J. 'Beneficial Effect of Acupuncture on Depression.' Acupuncture Therapy for Neurological Diseases. Springer. 2010; 437-39.

Han C, Li X, Luo H, Zho X, and Li X. 'Clinical Study on Electroacupuncture Treatment for 30 Cases of Mental Depression.' Journal of Traditional Chinese Medicine. 2004. 24(3): 172-6.

Meng F, Luo H, Shen Y, Shu L, & Liu J. 'Plasma NE Concentrations and 24 Hours Urinary MHPG SO4 Excretion Changes After Electro-Acupuncture Treatment in Endogenous Depression.' World J. Acup-Mox. 1994; 4:45-52.

Jin GL, Zhou DF & Su J. 'The effect of electro-acupuncture on chronic stress-induced depression rat brain's monoamine neurotransmitters.' Chin J Psychiatry. 1999; 32: 220-222.

Han C, Li X & Luo H. Randomized clinical trial comparing the effects of elctro-acupuncture and maprotiline in treating depression. Int. J Clin Acupoint. 2006; 15(1): 7-14.

Luo H, Shen Y, Meng F, Jia Y, Zhao X, Guo H, & Feng X. 'Preliminary research on treatment of common mental disorders with computer controlled electroacupuncture.' Chinese Journal of Integrated Medicine 1996; 2(2): 98-100.

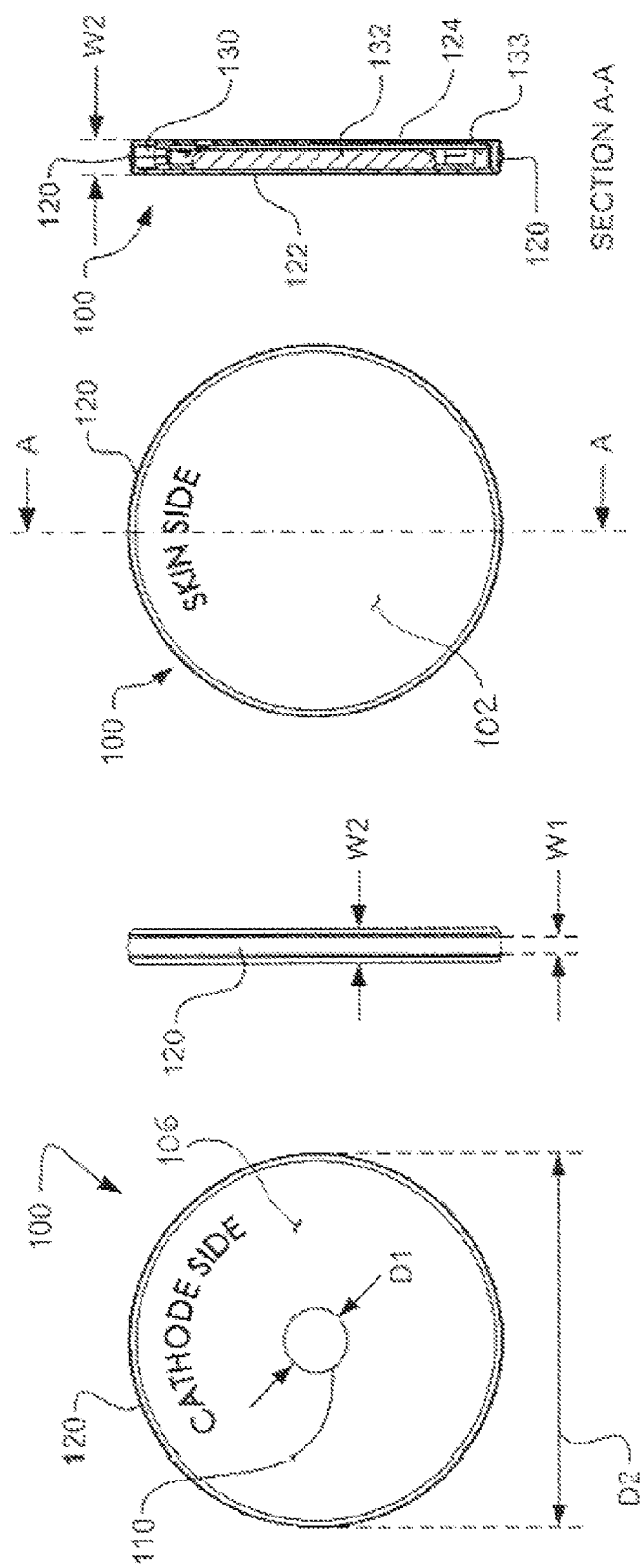

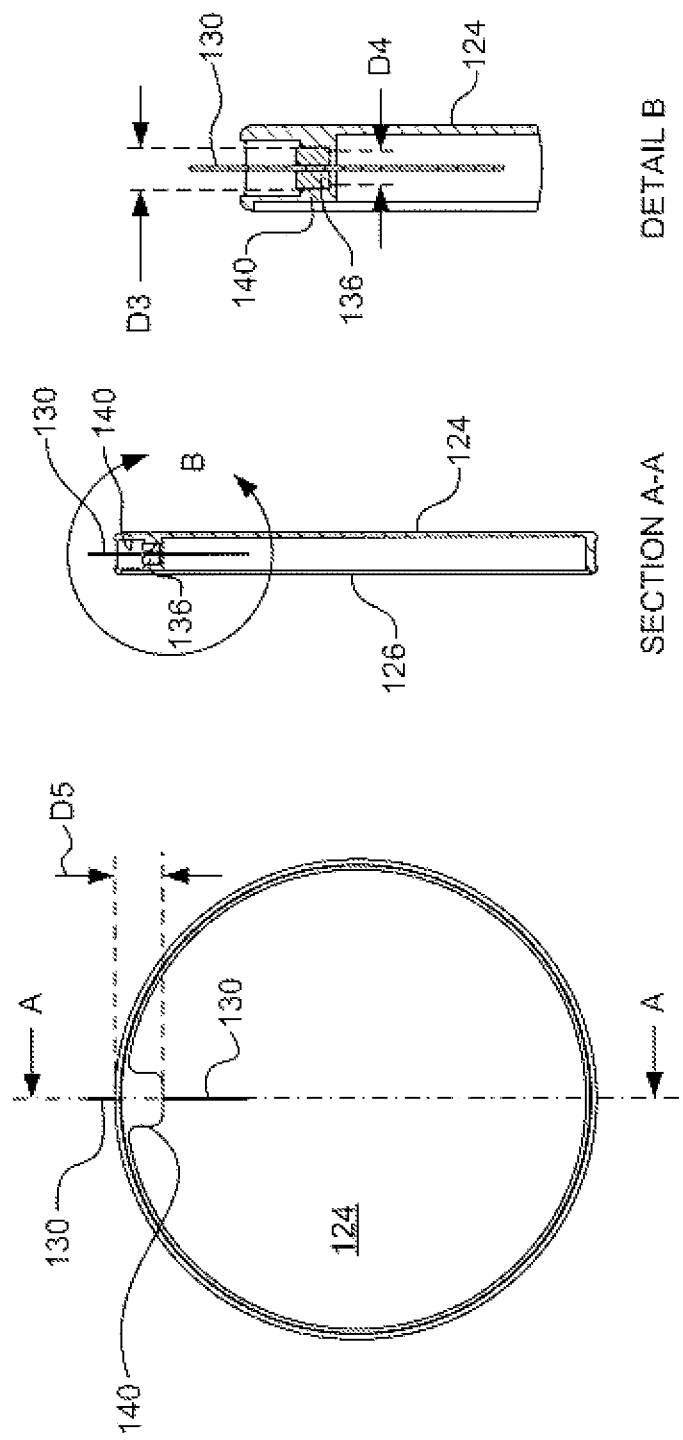

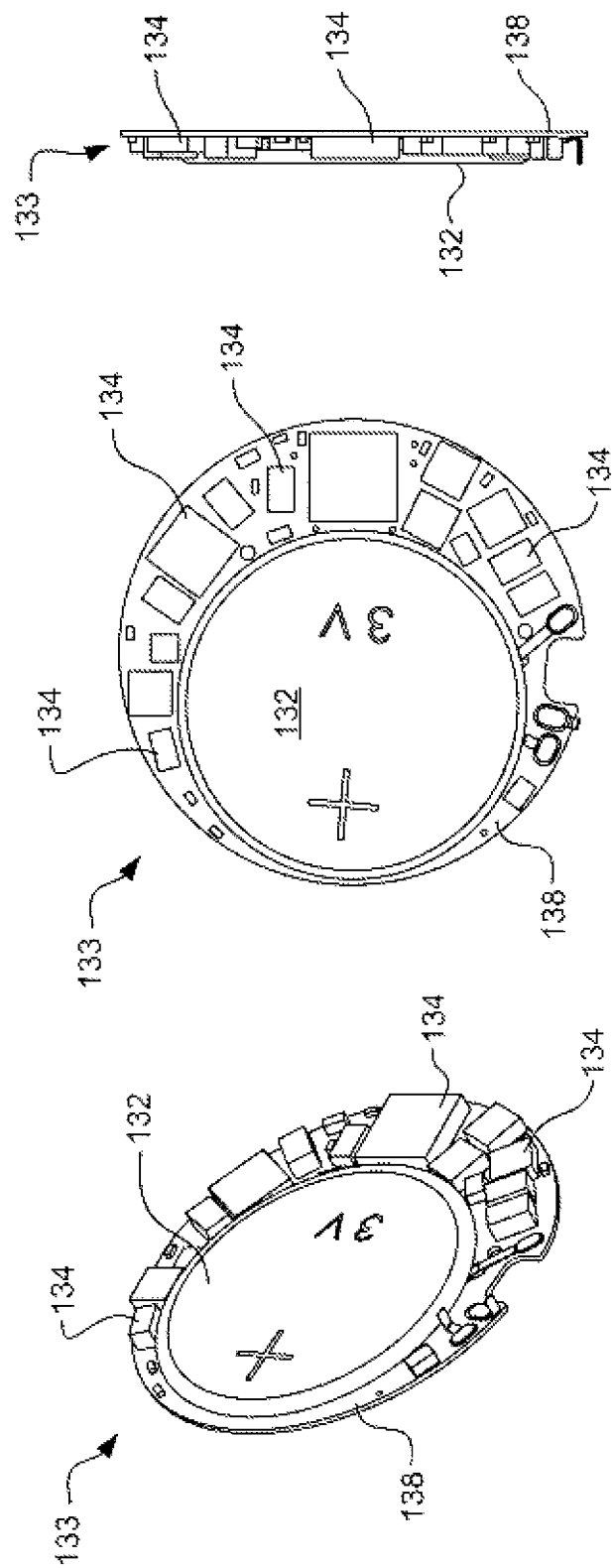

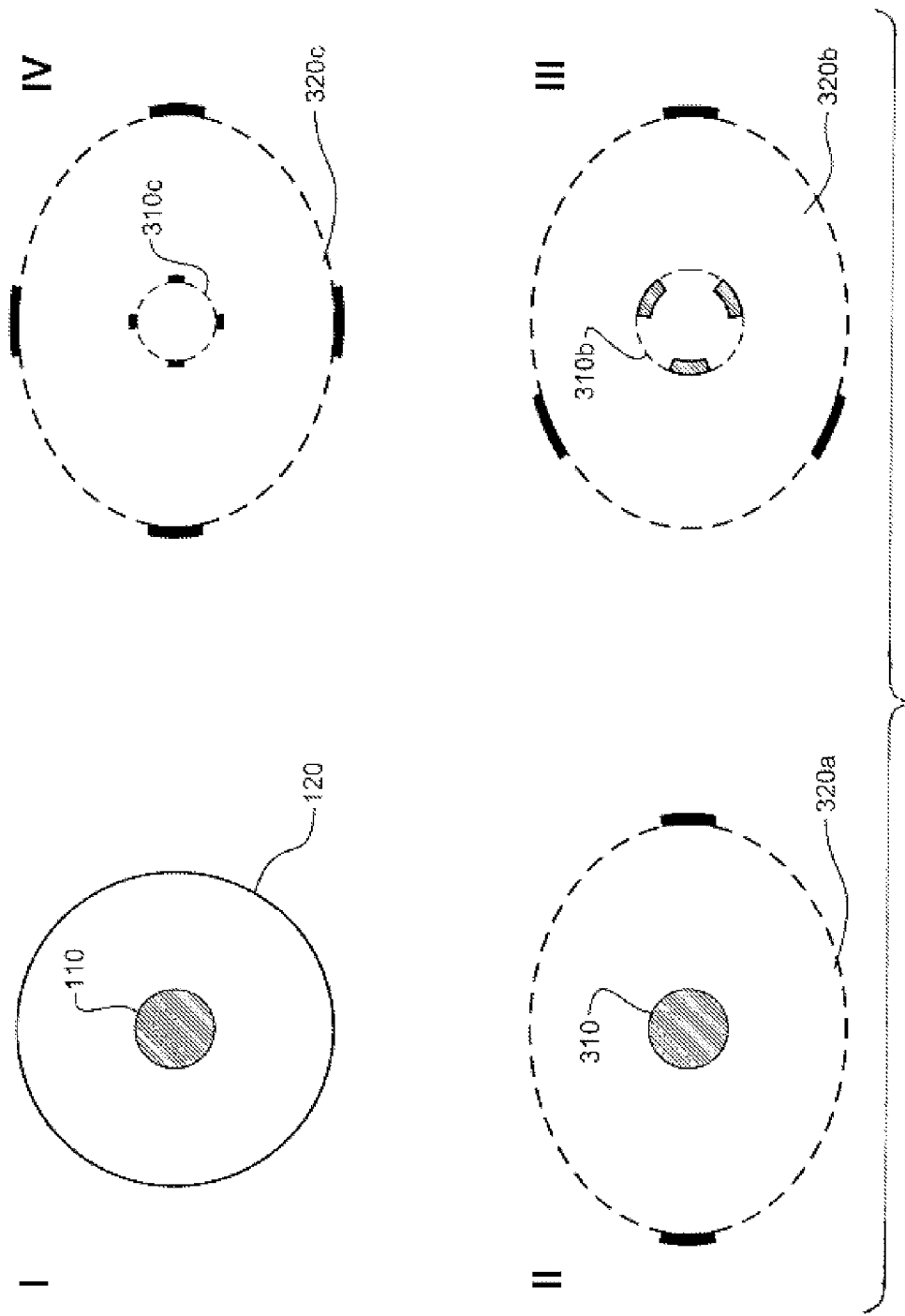

TABLE 1. Conditions Treated through Indicated Target Tissue Locations and Stimulation Regimen Parameters**

| Condition or Illness Treated | Acupoint(s)* (Target Tissue Locations) | T3 (min) | T4 (days) | T1 (msec) | T2 (msec) | A1 (volts) | A1 (mA) |
|---|---|---|---|---|---|---|---|
| Hypertension | PC5, PC6, ST36, ST37, LI4, LI11, LR3, GB34 | 10 - 60 | ½ - 14 | 0.1-2.0 | 200 - 2000 | 1 - 15 | 1 - 25 |
| Cardiovascular Disease | PC6 (or on an axis line connecting PC6 with either PC5 or PC7), ST36, BL14, HT7, EXHN1, HT5, LI11, LU2, LU7 (or underlying nerves) | 10 - 60 | ½ - 14 | 0.1 - 1.0 | 250 - 1000 | 1 - 15 | 1 - 25 |
| Depression | GV20, EXHN3 or underlying nerves (e.g., trigeminal nerve or three branches of trigeminal nerve) | 10 - 70 | 1 - 14 | 0.1 - 1.0 | 100 - 1000 | 1 - 15 | 1 - 25 |
| Bipolar Disorder | GV20, EXHN3 or underlying nerves | 10 - 70 | 1 - 14 | 0.1 - 1.0 | 250 - 1000 | 1 - 15 | 1 - 25 |
| Anxiety | GV20, EXHN3 or underlying nerves | 10 - 70 | ½ - 14 | 0.1 - 1.0 | 100 - 1000 | 1 - 15 | 1 - 25 |
| Obesity | SP4, LR8, ST40, ST36, ST37, SP6, SP9, KI6 | 20 - 60 | ½ - 14 | 0.1 - 1.0 | 250 - 1000 | 1 - 15 | 1 - 25 |
| Dyslipidemia | ST40, ST36, SP4, ST37, LR8, SP6, SP9, KI6 | 20 - 60 | 1 - 14 | 0.1 - 1.0 | 250 - 1000 | 1 - 15 | 1 - 25 |
| Parkinson's Disease | GV20, GB34 or underlying nerves | 10 - 60 | 1 - 14 | 0.1 - 2.0 | 67 - 1000 | 1 - 15 | 1 - 25 |
| Essential Tremor | GV20, GB34 or underlying nerves | 10 - 60 | 1 - 14 | 0.1 - 2.0 | 67 - 1000 | 1 - 15 | 1 - 25 |
| Erectile Dysfunction | BL52, BL23, GV4 | 20 - 60 | 1 - 14 | 0.1 - 2.0 | 67 - 1000 | 1 - 20 | 1 - 25 |

*Bold font indicates a preferred target
**Duty Cycle of T3/T4 ≤ 0.05 prevents long values of T3 and/or short values of T4 in some instances

FIG. 18

IMPLANTABLE ELECTROACUPUNCTURE DEVICE AND METHOD

RELATED APPLICATIONS

This application is a Continuation-In-Part (CIP) of U.S. patent application Ser. No. 13/598,582, filed Aug. 29, 2012; U.S. patent application Ser. No. 13/622,653, filed Sep. 19, 2012; and U.S. patent application Ser. No. 13/630,522, filed Sep. 28, 2012; which applications are incorporated herein by reference. This application also claims the benefit of the following previously-filed provisional patent applications, each of which is also incorporated herein by reference:

1. Boost Converter Output Control For Implantable Electroacupuncture Device, filed Mar. 12, 2012, Appl. No. 61/609,875;
2. Boost Converter Circuit Surge Control For Implantable Electroacupuncture Device Using Digital Pulsed Shutdown, filed Jul. 16, 2012, Appl. No. 61/672,257;
3. Smooth Ramp-Up Stimulus Amplitude Control For Implantable Electroacupuncture Device, filed Jul. 17, 2012, Appl. No. 61/672,661;
4. Battery Transient Current Reduction In An Implantable Electroacupuncture Device, filed Jul. 19, 2012, Appl. No. 61/673,254;
5. Pulse Charge Delivery Control In An Implantable Electroacupuncture Device, filed Jul. 23, 2012, Appl. No. 61/674,691;
6. Radial Feed-Through Packaging For An Implantable Electroacupuncture Device, filed Jul. 26, 2012, Appl. No. 61/676,275.

BACKGROUND

Acupuncture has been practiced in Eastern civilizations (principally in China, but also in other Asian countries) for at least 2500 years. It is still practiced today throughout many parts of the world, including the United States and Europe. A good summary of the history of acupuncture, and its potential applications may be found in Cheung, et al., "*The Mechanism of Acupuncture Therapy and Clinical Case Studies*", (Taylor & Francis, publisher) (2001) ISBN 0-415-27254-8, hereafter referred to as "Cheung, Mechanism of Acupuncture, 2001." The Forward, as well as Chapters 1-3, 5, 7, 8, 12 and 13 of Cheung, *Mechanism of Acupuncture, 2001*, are incorporated herein by reference.

Despite the practice in Eastern countries for over 2500 years, it was not until President Richard Nixon visited China (in 1972) that acupuncture began to be accepted in the West, such as the United States and Europe. One of the reporters who accompanied Nixon during his visit to China, James Reston, from the *New York Times*, received acupuncture in China for post-operative pain after undergoing an emergency appendectomy under standard anesthesia. Reston experienced pain relief from the acupuncture and wrote about it in *The New York Times*. In 1973 the American Internal Revenue Service allowed acupuncture to be deducted as a medical expense. Following Nixon's visit to China, and as immigrants began flowing from China to Western countries, the demand for acupuncture increased steadily. Today, acupuncture therapy is viewed by many as a viable alternative form of medical treatment, alongside Western therapies. Moreover, acupuncture treatment is now covered, at least in part, by most insurance carriers. Further, payment for acupuncture services consumes a not insignificant portion of healthcare expenditures in the U.S. and Europe. See, generally, Cheung, *Mechanism of Acupuncture*, 2001, vii.

Acupuncture is an alternative medicine that treats patients by insertion and manipulation of needles in the body at selected points. See, Novak, Patricia D. et al (1995). Dorland's Pocket Medical Dictionary (25th ed.), Philadelphia: (W.B. Saunders Publisher), ISBN 0-7216-5738-9. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: http://www.acupuncturehealing.org/acupuncture-points-map.html. Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter typically refers to a body organ, or meridian, or other tissue location associated with, or affected by, that acupoint. However, usually only the letter is used in referring to the acupoint, but not always. Thus, for example, the acupoint BL23 is the same as acupoint Bladder 23 which is the same as BL-23 which is the same as BL 23 which is the same as Shenshu. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies most all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations* 2008"). For the convenience of the reader, the Table of Contents, Forward (page v-vi) and General Guidelines for Acupuncture Point Locations (pages 1-21), as well as pages 26, 29, 35, 39, 64, 66, 71-72, 74, 84-85, 106, 111, 125, 138, 154-155, 188, 197, 199, 205, 213 (which illustrate with particularity the location of selected acupoints referenced herein), are submitted herewith as Appendix D. The entire book, WHO Standard Acupuncture Point Locations 2008, is incorporated herein by reference.

While many in the scientific and medical community are highly critical of the historical roots upon which acupuncture has developed, (e.g., claiming that the existence of meridians, qi, yin and yang, and the like have no scientific basis), see, e.g., http://en.wikipedia.org/wiki/Acupuncture, few can refute the vast amount of successful clinical and other data, accumulated over centuries of acupuncture practice, that shows needle manipulation applied at certain acupoints is quite effective.

The World Health Organization and the United States' National Institutes of Health (NIH) have stated that acupuncture can be effective in the treatment of neurological conditions and pain. Reports from the USA's National Center for Complementary and Alternative Medicine (NCCAM), the American Medical Association (AMA) and various USA government reports have studied and commented on the efficacy of acupuncture. There is general agreement that acupuncture is safe when administered by well-trained practitioners using sterile needles, but not on its efficacy as a medical procedure.

An early critic of acupuncture, Felix Mann, who was the author of the first comprehensive English language acupuncture textbook *Acupuncture: The Ancient Chinese Art of Healing*, stated that "The traditional acupuncture points are no more real than the black spots a drunkard sees in front of his eyes." Mann compared the meridians to the meridians of longitude used in geography—an imaginary human construct. Mann, Felix (2000). *Reinventing acupuncture: a new concept of ancient medicine*. Oxford: Butterworth-Heinemann. pp. 14; 31. ISBN 0-7506-4857-0. Mann attempted to combine his medical knowledge with that of Chinese theory. In spite of his protestations about the theory, however, he apparently believed there must be something to it, because he was fascinated by it and trained many people in the West with the parts of it he borrowed. He also wrote many books on this subject. His legacy is that there is now a college in London and a system of needling that is known as "Medical Acupuncture". Today this college trains doctors and Western medical professionals only.

For purposes of this patent application, the arguments for and against acupuncture are interesting, but not that relevant. What is important is that a body of literature exists that identifies several acupoints within the human body that, rightly or wrongly, have been identified as having an influence on, or are otherwise somehow related to, the treatment of various physiological conditions, deficiencies or illnesses. With respect to these acupoints, the facts speak for themselves. Either these points do or do not affect the conditions, deficiencies or illnesses with which they have been linked. The problem lies in trying to ascertain what is fact from what is fiction. This problem is made more difficult when conducting research on this topic because the insertion of needles, and the manipulation of the needles once inserted, is more of an art than a science, and results from such research become highly subjective. What is needed is a much more regimented approach for doing acupuncture research.

It should also be noted that other medical research, not associated with acupuncture research, has over the years identified nerves and other locations throughout a patient's body where the application of electrical stimulation produces a beneficial effect for the patient. Indeed, the entire field of neurostimulation deals with identifying locations in the body where electrical stimulation can be applied in order to provide a therapeutic effect for a patient. For purposes of this patent application, such known locations within the body are treated essentially the same as acupoints—they provide a "target" location where electrical stimulation may be applied to achieve a beneficial result, whether that beneficial result is to treat erectile dysfunction, reduce cholesterol or triglyceride levels, to treat cardiovascular disease, to treat mental illness, or to address some other issue associated with a disease or condition of the patient.

Returning to the discussion regarding acupuncture, some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to Acupuncture Today, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004-02-01 (retrieved on-line 2006-08-09 at http://www.acupuncturetoday.com/abc/electroacupuncture.php).

U.S. Pat. No. 7,203,548, issued to Whitehurst et al., discloses use of an implantable miniature neurostimulator, referred to as a "microstimulator," that can be implanted into a desired tissue location and used as a therapy for cavernous nerve stimulation. The microstimulator has a tubular shape, with electrodes at each end.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,950,707 (obesity and eating disorders); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagus nerve with both electrical stimulation and drugs); U.S. Pat. No. 7,292,890 (Vagus nerve stimulation); U.S. Pat. No. 6,735,745 (headache and/or facial pain); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain). The microstimulator patents either require electronics and battery in a coil on the outside of the body or a coil on the outside that enables the recharging of a rechargeable battery. The use of an outside coil, complex electronics, and the tubular shape of the microstimulator have all limited the commercial feasibility of the microstimulator device and applications described in the Whitehurst patents.

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize (i) large implantable stimulators having long leads that must be tunneled through tissue over an extended distance to reach the desired stimulation site, (ii) external devices that must interface with implanted electrodes via percutaneous leads or wires passing through the skin, or (iii) inefficient and power-consuming wireless transmission schemes. Such devices and methods are still far too invasive, or are ineffective, and thus are subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purpose of treating erectile dysfunction.

SUMMARY

One characterization of the invention described herein is that of an Implantable ElectroAcupuncture Device (IEAD)

adapted to treat a specified medical condition of a patient through application of stimulation pulses applied substantially at or near a specified target tissue location. Such IEAD includes: (a) a small IEAD housing having an electrode configuration thereon that includes at least two electrodes/arrays, the longest liner dimension of the small IEAD housing being no greater than about 25 mm, and the shortest linear dimension, measured orthogonal to the longest linear dimension, is no greater than about 2.5 mm, wherein at least one of the at least two electrodes/arrays comprises a central electrode/array located substantially in the center of a first surface of the IEAD housing, and wherein at least another of the at least two electrodes/arrays comprises a circumferential electrode/array located substantially around and at least 5 mm distant from the center of the central electrode/array, wherein the first surface (106) of the IEAD housing when implanted is adapted to face inwardly into the patient's tissue at or near the specified target tissue location; (b) pulse generation located within the IEAD housing and electrically coupled to the at least two electrodes/arrays, wherein the pulse generation circuitry is adapted to deliver stimulation pulses to the patient's body tissue at or near the target tissue location in accordance with a specified stimulation regimen, the stimulation regimen defining a duration (T3) and rate (1/T4) at which a stimulation session is applied to the patient, the stimulation regimen requiring that the stimulation session have a duration of T3 minutes and a rate of occurrence of once every T4 minutes, wherein the ratio of T3/T4 is no greater than 0.05, and wherein during each stimulation session stimulation pulses having one or more specified widths (T1) and amplitudes (A1) are generated at one or more specified rates (1/T2); (c) a primary battery contained within the IEAD housing and electrically coupled to the pulse generation circuitry that provides operating power for the pulse generation circuitry, the primary battery having a nominal output voltage of 3 volts, and an internal impedance greater than 5 ohms; and (d) a sensor contained within the IEAD housing responsive to operating commands wirelessly communicated to the IEAD from a non-implanted location, said operating commands allowing limited external control of the IEAD.

The specified medical condition, in accordance with some embodiments of the invention, includes at least one of (1) hypertension, (2) cardiovascular disease, (3) depression, (4) bipolar disorder, (5) Anxiety, (6) obesity, (7) dyslipidemia, (8) Parkinson's disease, (9) Essential tremor, or (10) erectile dysfunction. Moreover, in other embodiments of the invention where at least one of the specified medical conditions is used, the specified target tissue location comprises at least one acupoint selected from the group of acupoints comprising: BL14, BL23, BL52, EXHN1, EXHN3, GB34, GV4, GV20, HT5, HT7, KI6, LI4, LI11, LR3, LR8, LU2, LU7, PC5, PC6, PC7, SP4, SP6, SP9, ST36, ST37, and ST40.

In accordance with another embodiment, the invention described herein may be characterized as a an implantable electroacupuncture device (IEAD) adapted to generate and apply electrical stimulus pulses to a target tissue location of a patient when the IEAD is implanted at or near a target tissue location. This embodiment of the invention includes: (a) an hermetically sealed case having a linear dimension in first plane no greater than about 25 mm, and a linear dimension in a second plane orthogonal to the first plane no greater than about 2.5 mm; (b) at least anodic electrode and at least one cathodic electrode secured to an outside surface of the hermetically sealed case, the separation between the point where the cathodic electrode is closest to the anodic electrode being at least 5 mm; (c) electronic circuitry housed within the hermetically sealed case that causes electrical stimulus pulses to be generated and applied to the at least one cathodic electrode and the at least one anodic electrode in accordance with a prescribed stimulation regime: (d) means for electrically connecting the electronic circuitry on the inside of the hermetically sealed case to the at least two electrodes on the outside of the hermetically sealed case; and (e) a primary battery on the inside of the hermetically sealed case connected to the electronic circuitry that provides operating power for the electronic circuitry, the primary battery having a nominal output voltage of $V_{BAT}$ volts, where $V_{BAT}$ ranges from as low 2.2 volts to as high as 3.6 volts. The primary battery has an internal impedance greater than 5 ohms. Additionally, the electronic circuitry includes power management circuitry that limits the amount of instantaneous current that can be drawn from the battery. Further, the electronic circuitry is able to control the generation of the electrical stimulus pulses so that the stimulus pulses are applied only during a stimulation session having a duration of T3 minutes, and wherein the time interval between stimulation sessions is T4 minutes, and wherein the ratio of T3/T4 is maintained at a value that is no greater than 0.05.

The invention herein described may also be characterized as a method for operating an implantable electroacupuncture device (IEAD) powered only by a thin, coin-cell type battery having an internal impedance greater than 5 ohms, over a period of at least 2 years, during which time the IEAD is adapted to generate stimulus pulses during a stimulation session in accordance with a prescribed stimulation regimen. Such method includes the steps of: (a) powering pulse generation circuitry within the IEAD with the coin-cell type battery; (b) limiting the duration of stimulation sessions during which stimulus pulses are generated to a time period that has a duty cycle of less than 0.05, where the duty cycle is the ratio of T3 to T4, where T3 is the duration of the stimulation session, and where T4 is the time interval between stimulation sessions; (c) boosting the battery voltage from the coin-cell type battery using a boost converter circuit by a factor of at least 4 in order to provide sufficient operating power to generate current stimulus pulses of up to 25 mA during a stimulation session; and (d) limiting the instantaneous current that can be drawn from the coin-cell type battery to prevent the battery voltage, $V_{BAT}$, from dropping below safe operating levels.

Additionally, the invention described herein may be characterized as a method of assembling an implantable electroacupuncture device (IEAD) for use in treating a specified medical condition of a patient. The IEAD is assembled so as to reside in a round, thin, hermetically-sealed, coin-sized housing. An important feature of the coin-size housing, and the method of assembly associated therewith, is that the method electrically and thermally isolates a feed-through pin assembly radially passing through a wall of the coin-sized housing from the high temperatures associated with welding the housing closed to hermetically seal its contents. Such method of assembling includes the steps of:

a. forming a coin-sized housing having a bottom case and a top cover plate, the top cover plate being adapted to fit over the bottom case, the bottom case being substantially round and having a diameter D2 that is nominally 23 mm and a perimeter side wall extending all the way around the perimeter of the bottom case, the perimeter side wall having a height W2, wherein the ratio of W2 to D2 is no greater than about 0.13;

b. forming a recess in one segment of the side wall, the recess extending radially inwardly from the side wall to a depth D3, and the recess having an opening in a bottom wall portion thereof;

c. hermetically sealing a feed-through assembly in the opening in the bottom of the recess, the feed-through assembly having a feed-through pin that passes through the opening without contacting the edges of the opening, a distal end of the pin extending radially outward beyond the side wall of the bottom case, and a proximal end of the feed-through pin extending radially inward toward the center of the bottom case, whereby the feed-through pin assembly is hermetically bonded to the opening in the side wall at a location in the bottom of the recess that is a distance D3 from the perimeter side wall, thereby thermally isolating the feed-through assembly from the high temperatures that occur at the perimeter side wall when the cover plate is welded to the edge of the perimeter side wall;

d. attaching a central electrode to the thin, coin-sized housing at a central location on the bottom outside surface of the feed-through housing;

e. inserting an electronic circuit assembly, including a battery, inside of the bottom case, and connecting the proximal end of the feed-though pin to an output terminal of the electronic circuit assembly, and electrically connecting the bottom case to a reference terminal of the battery;

f. baking out the assembly to remove moisture, back filling with a mixture of He/Ar inert gas, and then welding the top cover plate to the edges of the side wall of the bottom case, thereby hermetically sealing the electronic circuit assembly, including the battery, inside of the thin, coin-sized IEAD housing;

g. leak testing the welded assembly to assure a desired level of hermeticity has been achieved;

h. placing an insulating layer of non-conductive material around the perimeter edge of the thin coin-sized housing, then placing a circumscribing electrode over the insulating layer of non-conductive material, and then electrically connecting the distal end of the feed-through pin to the circumscribing electrode; and i. covering all external surface areas of the thin, coin-sized housing with a layer of non-conductive material except for the circumscribing electrode around the perimeter of the coin-sized housing and the central electrode centrally located on the bottom surface of the thin-coin-sized housing.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of one surface, indicated as the "Cathode Side," of the IEAD housing illustrated in FIG. 1.

FIG. 2A shows a side view of the IEAD housing illustrated in FIG. 1.

FIG. 3 shows a plan view of the other side, indicated as the "Skin Side," of the IEAD housing or case illustrated in FIG. 1.

FIG. 3A is a sectional view of the IEAD of FIG. 3 taken along the line A-A of FIG. 3.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, adapted to fit inside of the empty housing of FIG. 4 and FIG. 5.

FIGS. 6A and 6B show a plan view and side view, respectively, of the electronic assembly shown in FIG. 6.

FIG. 7A schematically illustrates a few alternative electrode configurations that may be used with the IEAD.

FIG. 18 is a table that summarizes various acupoints or other target tissue locations that may be stimulated with stimulation pulses provided by an IEAD implanted at or near the target tissue locations in order to treat or provide therapy for the conditions indicated.

Figure 1:
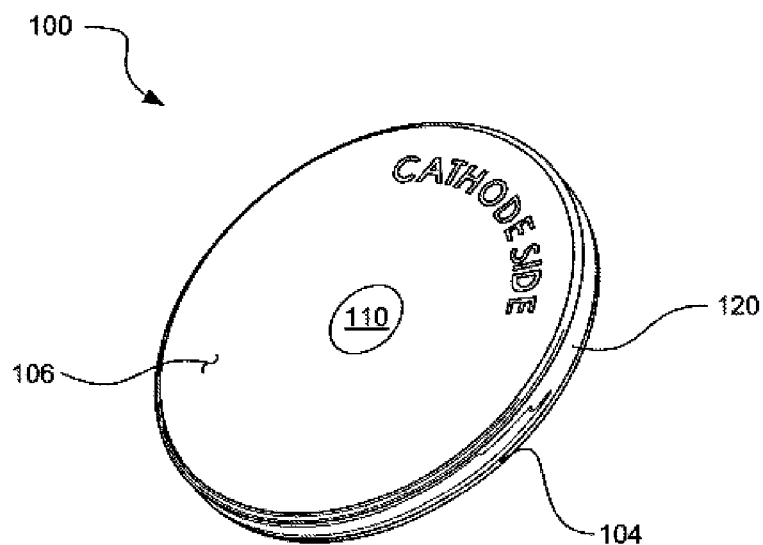
FIG. 1 is a perspective view of an Implantable Electroacupuncture Device (IEAD) made in accordance with the teachings presented herein.

Appendix A illustrates some examples of alternate symmetrical electrode configurations that may be used with an IEAD of the type described herein.

Appendix B illustrates a few examples of non-symmetrical electrode configurations that may be used with an IEAD made in accordance with the teachings herein.

Appendix C shows an example of the code used in the micro-controller IC (e.g., U2 in FIG. 14A) to control the basic operation and programming of the IEAD, e.g., to turn the IEAD ON/OFF, adjust the amplitude of the stimulus pulse, and the like, using only an external magnet as an external communication element.

Appendix D contains selected pages from the book *WHO Standard Acupuncture Point Locations* 2008.

Appendices A, B, C and D are submitted herewith and are incorporated by reference herein.

Throughout the drawings and appendices, identical reference numbers designate similar, but not necessarily identical, elements.

DETAILED DESCRIPTION

Overview

Disclosed and claimed herein is an implantable, self-contained, leadless electroacupuncture (EA) device having at least two electrode contacts mounted on the surface of its housing. The EA device disclosed herein, which is also referred to as an implantable electroacupuncture device (IEAD), is adapted to treat various medical conditions, deficiencies and illnesses of a patient when implanted at selected target tissue locations, e.g., acupoints, and when the IEAD is activated to provide EA stimulation at those target locations in accordance with a specified stimulation regimen. Ideally, the IEAD is coin-shaped and -sized, making it easy to implant.

In one preferred embodiment, the electrodes on the surface of the EA device include a central cathode electrode on a bottom side of the housing, and an annular anode electrode that surrounds the cathode. In another preferred embodiment, the annular anode electrode is a ring electrode placed around the perimeter edge of the coin-shaped housing.

The EA device is leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

The EA device is adapted to be implanted through a very small incision, e.g., less than 2-3 cm in length, directly adjacent to a selected target stimulation site, e.g., an acupuncture site ("acupoint"), known to affect or influence a particular medical condition or illness of a patient that needs to receive treatment.

The EA device is easy to implant. Also, most embodiments are symmetrical. This means that there is no way that it can be implanted incorrectly (unless the physician puts it in up-side-down, which would be difficult to do given the markings on its case). Once an incision has been made and an implant pocket has been prepared by skilled medical personnel, implantation of the IEAD is almost as easy as sliding a coin into a slot. Such implantation can usually be completed in less than 10 minutes in an outpatient setting, using only local anesthesia. When done properly, no major or significant complications should occur during or after the implant procedure. The EA device can also be easily and quickly explanted, if needed.

The EA device is self-contained. It includes a primary battery to provide its operating power. It includes all of the circuitry it needs, in addition to the battery, to allow it to perform its intended function for several years. Once implanted, the patient will not even know it is there, except for a slight tingling that may be felt when the device is delivering stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet.

The EA device can operate for several years because it is designed to be very efficient. Stimulation pulses applied by the EA device at a selected target stimulation site, e.g., a specified acupoint, through its electrodes formed on its case are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one preferred treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's medical condition that is being treated.

The EA device is, compared to most implantable medical devices, relatively easy to manufacture and uses few components. This not only enhances the reliability of the device, but keeps the manufacturing costs low, which in turn allows the device to be more affordable to the patient. One key feature included in the mechanical design of the EA device is the use of a radial feed-through assembly to connect the electrical circuitry inside of its housing to one of the electrodes on the outside of the housing. The design of this radial feed-through pin assembly greatly simplifies the manufacturing process. The process places the temperature sensitive hermetic bonds used in the assembly—the bond between a pin and an insulator and the bond between the insulator and the case wall—away from the perimeter of the housing as the housing is hermetically sealed at the perimeter with a high temperature laser welding process, thus preserving the integrity of the hermetic bonds that are part of the feed-through assembly.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

Another key feature included in the design of the EA device is the use of a commercially-available battery as its primary power source. Small, thin, disc-shaped batteries, also known as "coin cells," are quite common and readily available for use with most modern electronic devices. Such batteries come in many sizes, and use various configurations and materials. However, insofar as the inventors or Applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible, and so that dips in the battery output voltage (caused by any sudden surge in instantaneous battery current) do not occur that could compromise the performance of the device. Furthermore, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Moreover, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture and to provide it to patients at an affordable cost.

DEFINITIONS

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular. "Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−1.15 mm (0.05×23 mm=1.15 mm). "Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, an important aspect of the invention recognizes that an electroacupuncture modulation scheme need not be continuous, thereby allowing the implanted EA device to use a small, high density, power source to provide such non-continuous EA modulation. (Here, it should be noted that "EA modulation," as that phrase is used herein, is the application of electrical stimulation pulses, at low intensities, low frequencies and low duty cycles, to at least one of the target stimulation sites, e.g., an acupuncture site that has been identified as affecting a particular condition of the patient. As a result, the EA device can be very small. And, because the electrodes form an integral part of the housing of the EA device, the EA device may thus be implanted directly at (or very near to) the desired target tissue location, e.g., the target stimulation site, such as the target acupoint.

In summary, the basic approach of EA stimulation disclosed herein includes: (1) identify an acupoint(s) or other target stimulation site that may be used to treat or mediate the particular illness, condition or deficiency that has manifest itself in the patient, e.g., erectile dysfunction; (2) implant an EA device, made as described herein, so that its electrodes are located to be near or on the identified acupoint(s) or other target stimulation site; (3) apply EA modulation, having a low intensity, low frequency, and low duty cycle through the electrode(s) of the EA device so that electrical stimulation pulses flow through the tissue at the target stimulation site following a prescribed stimulation regimen over several weeks or months or years. At any time during this EA stimulation regimen, the patient's illness, condition or deficiency may be evaluated and, as necessary, the parameters of the EA modulation applied during the EA stimulation regimen may be adjusted or "tweaked" in order to improve the results obtained from the EA modulation.

Conditions Treated

The IEAD disclosed herein may be used to treat many different medical conditions of a patient, including, inter alia, (1) hypertension, (2) cardiovascular disease, (3) depression, (4) bipolar disorder, (5) Anxiety, (6) obesity, (7) dyslipidemia, (8) Parkinson's disease, (9) Essential tremor, and (10) erectile dysfunction (ED). For each of these ten enumerated conditions, Applicant has performed extensive research in the acupuncture art to determine which acupoints are likely to be the best candidates for being modulated (i.e., stimulated with electroacupuncture pulses) in order to treat and/or provide some meaningful relief relative to symptoms of these conditions. This research is documented in some of Applicant's previously-filed patent applications, which other patent applications can be located by searching in the records of the U.S. Patent Office for patent applications of Valencia Technologies Corporation, of Valencia, Calif. As a result of this research, Applicant has identified at least one acupoint for each of the above-identified ten enumerated conditions/diseases, which at least one acupoint represents—insofar as the inventors are presently aware—the best candidate(s) for where EA stimulation from an IEAD of the type described herein should be applied for successful treatment of the condition/disease. Some overlap exists between the identified acupoints, i.e., in some instances the same acupoint(s) may be stimulated to treat multiple conditions. The results of this research are summarized in Table 1, shown in FIG. 18.

As seen in Table 1 (FIG. 18), the ten conditions are listed in the left column. The acupoint(s) that represents, based on Applicant's research, the best candidate(s) for applying electrical stimulation pulses in order to treat the indicated condition, is/are listed in the column of Table 1 labeled "Acupoints (Target Tissue Locations)". The nomenclature used in the reference book *WHO Standard Acupuncture Point Locations* 2008 is used to identify most of these acupoints. Moreover, selected pages from the *WHO Standard Acupuncture Point Locations* 2008 reference book that show detailed diagrams of where the identified acupoint(s) is/are located on the human body are included in Appendix D, submitted herewith. Finally, in the six columns on the right of Table 1, the stimulation parameters thought by the inventors at the present time to provide the most effective stimulation regimen for the identified acupoint(s) are set forth. The meaning of these parameters will become apparent from the description below under the heading "Locations Stimulated and Stimulation Paradigms/Regimens," as well as the description of the IEAD presented below in connection with the description of, e.g., FIGS. 8A, 10, 14A, 15A and 15B.

It should be noted that the ten conditions enumerated in Table 1 (FIG. 18) are only exemplary of a small set of conditions of what Applicant believes may eventually be a much larger set of conditions that can be treated by using an IEAD as described herein to apply electrical stimulation to selected target tissue locations throughout a patient's body. That is, the list of 10 conditions presented above, and shown in Table 1, is an "open" list, not a "closed" list. It is hoped that use of this device—the IEAD described herein—, or equivalents thereof, will prove to be a useful tool not only to provide needed treatment and relief for patients suffering from any of these enumerated conditions, but will also promote additional research that will identify many more conditions and associated target tissue locations whereat EA stimulation can be successfully applied.

In this regard, it should further be emphasized that "EA stimulation" or "EA modulation", as those terms are used herein, is not intended to limit the resulting electrical stimulation pulses to be applied at a specified acupoint. Rather, for purposes herein, "EA stimulation" or "EA modulation" is electrical stimulation that is applied to whatever target tissue stimulation point has been selected in a manner consistent with the teachings herein, i.e., at a very low duty cycle. This low duty cycle (less than 0.05) means using stimulation sessions that have a duration of 10-60 minutes, and where the stimulation sessions are applied no more than once a day, but usually only once a week or once every other week. Further, "EA stimulation" or "EA modulation" means, most of the time, using stimulation pulses during a stimulation session that are at a low frequency (e.g., 1 Hz to 15 Hz), low intensity (less than 25 mA amplitude), and narrow pulse width (e.g., from 0.1 to 2 m). Finally, "EA stimulation" or "EA modulation" means applying the electrical stimulation through electrodes that are either attached directly to the case of the EA device, or coupled to the EA device, i.e., the IEAD, through a very short lead. In other words, there are no needles inserted through the skin to reach the target stimulation site, as occurs in traditional acupuncture, or traditional electroacupuncture. Rather, everything associated with the applied EA stimulation is done with a device, and its electrodes, that is implanted.

Locations Stimulated and Stimulation Paradigms/Regimens

As indicated above, Applicant has identified the acupoints (or other target tissue locations) listed in Table 1 (FIG. 18) as most responsible in acupuncture studies and most ideal for application of its technological approach to treat the conditions indicated. A description of the acupoints listed in Table 1 can be found in the reference book: *WHO Standard Acupuncture Point Locations* 2008, previously incorporated herein by reference. See, also, Appendix D, submitted herewith, and incorporated herein by reference, which contains selected pages from this reference book.

The stimulation parameters associated with the EA stimulation that should be applied to at least one of the indicated acupoints or other target tissue locations for treatment of the specified condition are also shown or listed in Table 1. In general, these parameters are typical of low-frequency electroacupuncture. That is, the EA stimulation should be applied at a low frequency, low intensity, and narrow pulse width. The pulse width of the stimulation pulse is defined as a time T1. The time interval between the start of one stimulation pulse and the start of the next stimulation pulse is a time T2. The frequency, or rate of occurrence of the stimulation pulses is thus 1/T2, expressed in units of pulses/sec, or Hz. The ratio of T1/T2 should be no greater than about 0.03, and is usually less than 0.01, thus assuring a narrow stimulation pulse width. The intensity, or amplitude, of the stimulation pulses (measured in either voltage or current, i.e., units of volts or milliAmps, or mA) is defined as A1. If the stimulation session has a duration of T3 minutes, and the stimulation sessions occur only once every T4 minutes (which may be expressed in units of minutes, hours, days or weeks, but care must be exercised when determining the duty cycle, or T3/T4, to ensure that the same units are used for both T3 and T4), then the duty cycle is T3/T4, and, in accordance with the operation restrictions of Applicant's IEAD, should be (must be) no greater than 0.05 in order to preserve the stored power of the small battery carried inside of the IEAD, and allowing the IEAD to operate for several years.

In summary, it is to be emphasized that the duration and rate of occurrence of the EA stimulation pulses applied by the IEAD described herein are not arbitrary nor chosen haphazardly or by guesswork. Rather these parameters have been chosen after a careful examination of the reports of successful manual acupuncture studies.

As can be seen from Table 1 (FIG. 18), the duration T3 of the stimulation sessions for the ten conditions listed in Table 1 varies from as short as ten minutes to as long as about 70 minutes; the interval between stimulation sessions T4 varies from as short as ½ day to as long as 14 days. The stimulus pulses during a stimulation session have a pulse width T1 that is, in some instances, as short as 0.1 milliseconds (ms) and, in other instances, as long as 2 ms. The period between application of stimulus pulses varies from as short as 67 milliseconds (ms), corresponding to a rate of about 15 Hz, to as long as 1 second, corresponding to a rate of 1 Hz. The amplitude A1 of the stimulus pulses varies from as low as 1 mA to as much as 25 mA. The parameters T1, T2, T3, T4 and A1 define the stimulation paradigm or regimen that is applied by the IEAD at a selected target tissue location.

A representative pulse width of the stimulus pulse T1 is 0.5 ms. A representative period T2 for the stimulus pulse rate is 500 ms=0.5 seconds (rate=1/0.5=2 Hz). A representative duration of a stimulation session T3 is thirty minutes, and a representative rate of occurrence of the stimulation session T4 is once every week. (Note: duty cycle T3/T4=30 min/10,080 min=0.003.) A representative amplitude A1 of the stimulus pulse is, e.g., 15 mA, but can be set as high as 25 mA.

Mechanical Design

A perspective view of one preferred embodiment of an implantable electroacupuncture device (IEAD) 100 that may be used for the purposes described herein is shown in FIG. 1. The IEAD 100 is also sometimes referred to as an implantable electroacupuncture stimulator (IEAS). As seen in FIG. 1, the IEAD 100 has the appearance of a disc or coin, having a front side 106, a back side 102 (not visible in FIG. 1) and an edge side 104.

As used herein, the "front" side of the IEAD 100 is the side that is positioned so as to face the target stimulation point (e.g., the desired acupoint) where EA stimulation is to be applied when the IEAD is implanted. The front side 106 may also be referred to herein as the "cathode side" 106. The "back" side 102 is the side opposite the front side and is the side farthest away from the target stimulation point when the IEAD is implanted. The "back" side 102 may also be referred to herein as the "skin" side 102 because most of the time it is the side closest to the skin when the IEAD is implanted (but, as explained below in connection with FIG. 17B, not always). The "edge" of the IEAD is the side that connects or joins the front side to the back side. In FIG. 1, the IEAD 100 is oriented to show the front side 106 and a portion of the edge side 104.

Many of the features associated with the mechanical design of the IEAD 100 shown in FIG. 1 are the subject of Applicant's co-pending U.S. patent application Ser. No. 13/777,901, filed Feb. 28, 2013, entitled "Radial Feed Through Packaging for an Implantable Electroacupuncture Device," which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 106 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
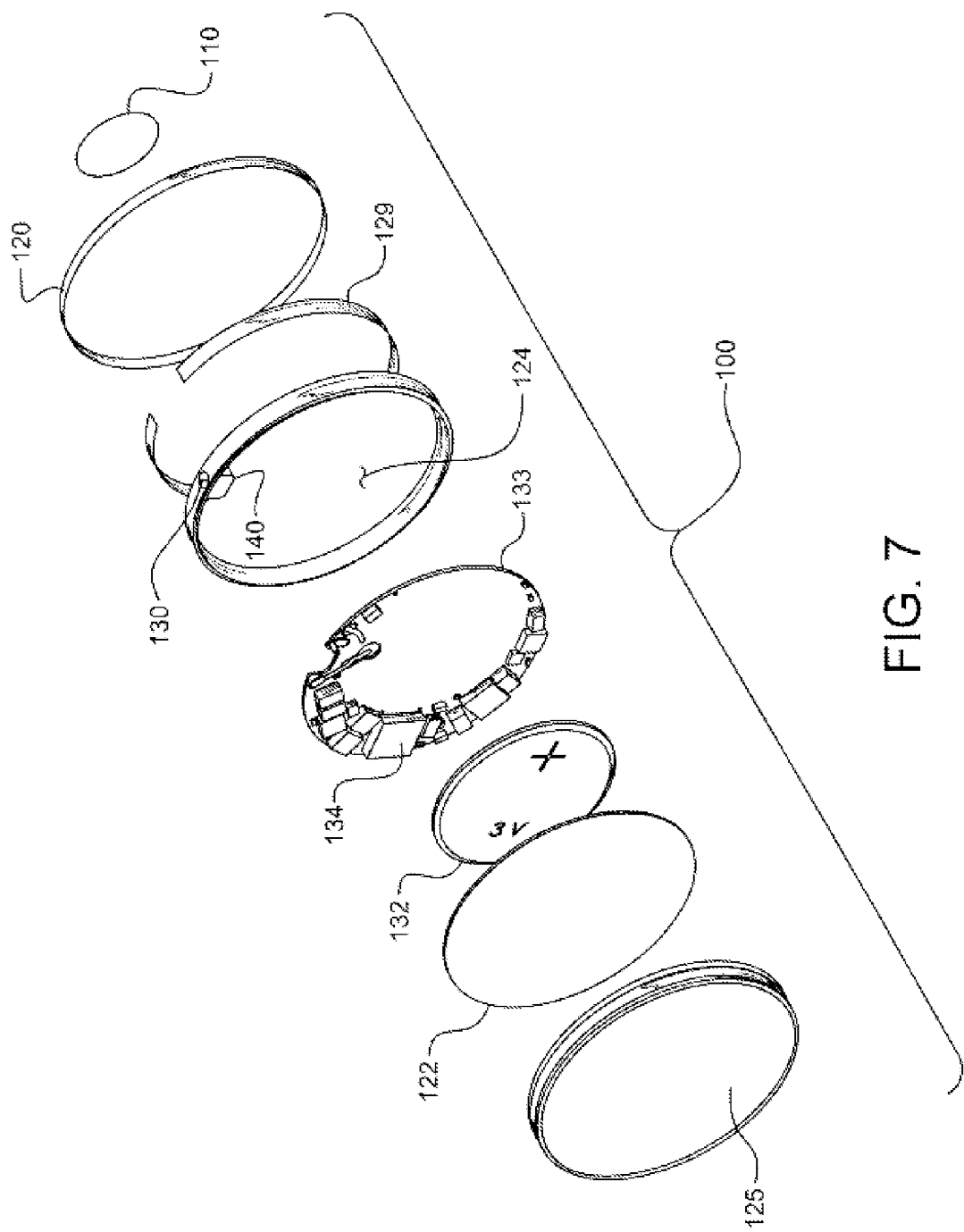
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the front side 106 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 106 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in Applicant's co-pending U.S. patent application Ser. No. 13/776,155, filed Feb. 25, 2013, entitled "Electrode Configuration for an Implantable Electroacupuncture Device," which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, faces the target tissue location that is to be stimulated. In addition, the IEAD must be implanted over the desired acupoint, or other tissue location, that is intended to receive the electroacupuncture (EA) stimulation. The orientation of the IEAD 100 is otherwise not important.

Figure 17A:
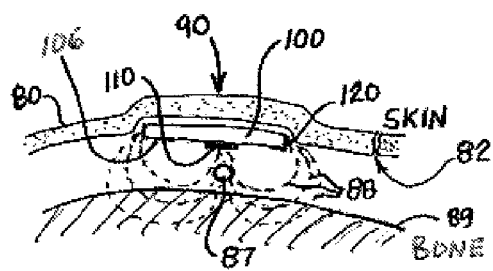
FIG. 17A shows a sectional view of a first way that an IEAD may be implanted at a selected target stimulation site when there is a bone or other skeletal structure that prevents the IEAD from being implanted very deep below the skin.
Figure 17B:
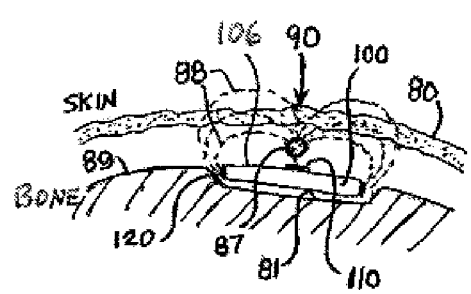
FIG. 17B shows a sectional view of a second way that an IEAD may be implanted at a selected target stimulation site when there is a bone or other skeletal structure that prevents the IEAD from being implanted very deep below the skin.
Figure 17:
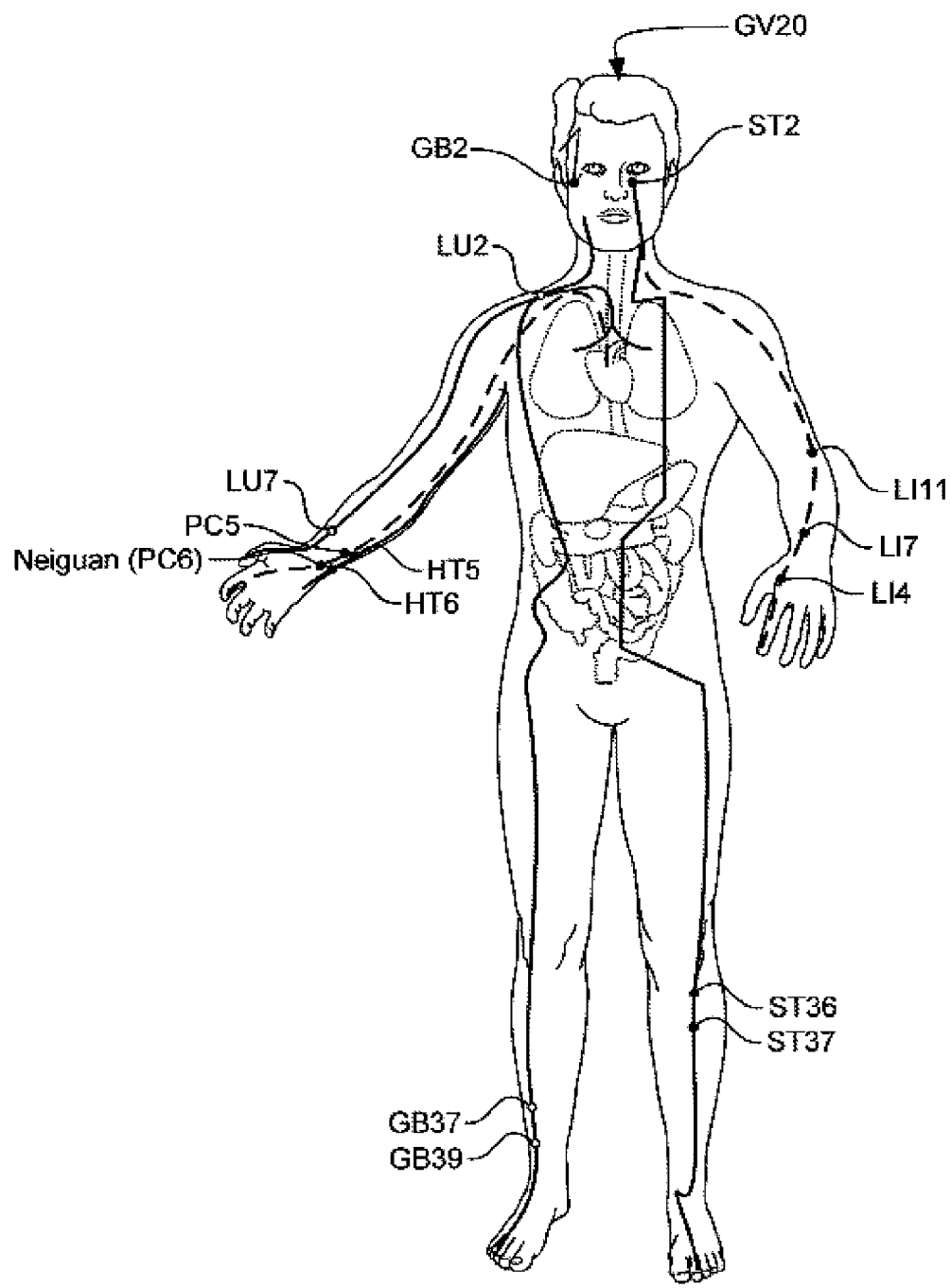
FIG. 17 illustrates various exemplary acupoints on a patient's body.

Turning next to FIG. 17, a representation of a human patient is depicted showing the location of several acupoints on the patient's body. As the reference book *WHO Standard Acupuncture Point Locations* 2008 teaches, and as is known in the art, the acupoints shown in FIG. 17 represent only a very small number of the total number of acupoints that have been identified on the human body. Any of these acupoints (those shown and not shown in FIG. 17), as well as other target tissue locations, such as nerves or muscle fibers, could be designated as the target stimulation point for use by the IDEA described herein.

Figure 1A:
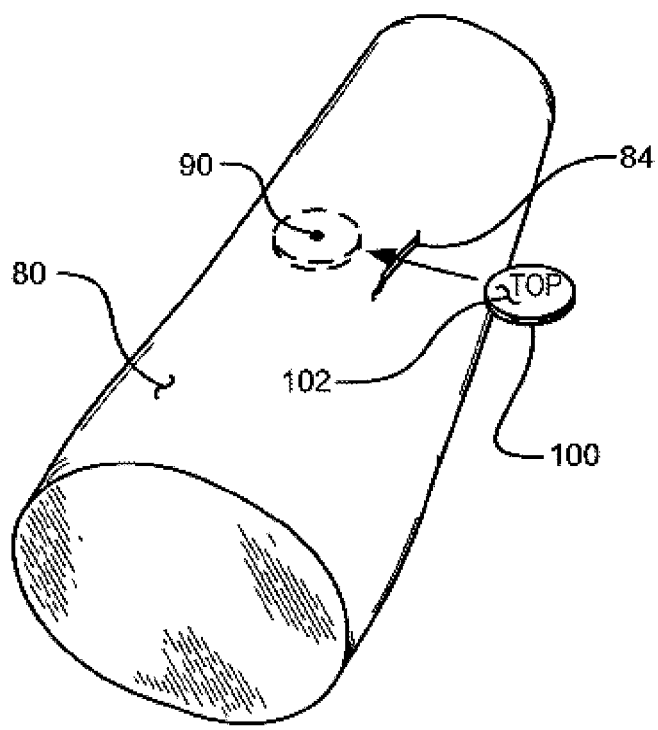
FIG. 1A illustrates the location of an exemplary acupoint (target stimulation site) on a limb of a patient, and illustrates one way in which an implantable electroacupuncture device (IEAD) of the type disclosed herein may be implanted at the target stimulation site for the purpose of providing electroacupuncture (EA) stimulation at that site.

For example, FIG. 1A illustrates the location of an exemplary target stimulation point 90, e.g. a point on a limb 80 of the patient, whereat the IEAD of FIG. 1 may be implanted for the treatment of a particular disease or condition of the patient. Such location is representative of a wide variety of acupoints, or other target tissue locations, where the IEAD of FIG. 1 could be implanted.

Figure 1B:
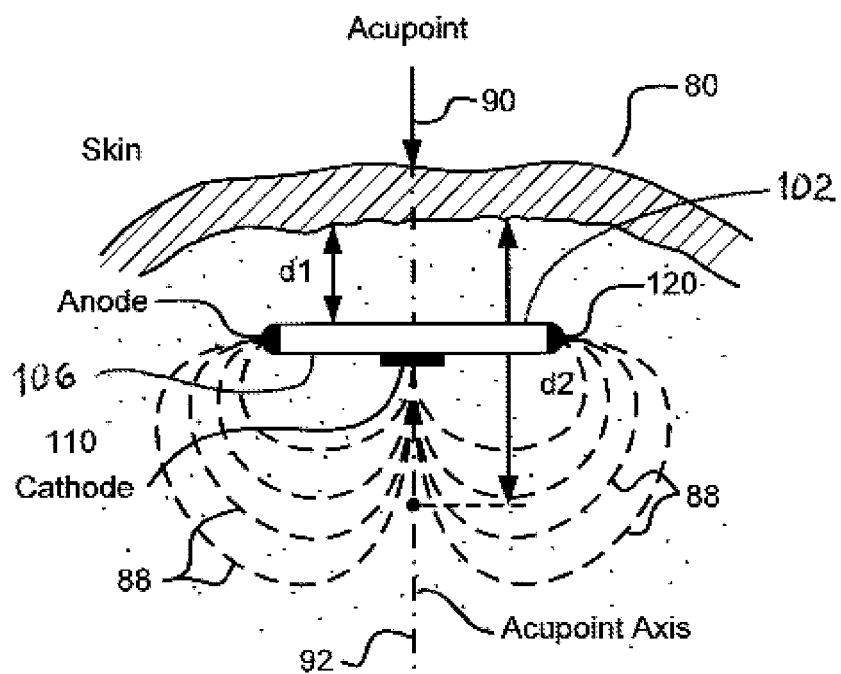
FIG. 1B shows a sectional view of an IEAD implanted at a selected target stimulation site, and illustrates the electric field gradient lines created when electroacupuncture (EA) stimulation pulses are applied to the tissue through electrodes attached to the surface of the IEAD housing.

An implanted IEAD 100 is illustrated generally in FIGS. 1A and 1B. Shown in FIG. 1B is a sectional view of the limb 80, or other body tissue, of the patient wherein a target tissue location 90 has been identified that is to receive electroacupuncture (EA) treatment using the IEAD 100. An incision 84 (shown in FIG. 1A) is made into the limb 80 a short distance, e.g., 10-15 mm, away from the target tissue location 90. A slot (e.g., parallel to the limb or tissue) is formed at the incision by lifting the skin closest to the acupoint up at the incision. As necessary, the surgeon may form a pocket under the skin at the acupoint location. The IEAD 100, with its top side 102 being closest to the skin (and thus also referred to as the "Skin Side"), is then carefully slid through the slot 84 into the pocket so that the center of the IEAD is located under the point 90 on the skin surface. This implantation process can be as easy as inserting a coin into a slot. With the IEAD 100 in place, the incision is sewn or otherwise closed, leaving the IEAD 100 under the skin 80 at the location of the target point 90 where electroacupuncture (EA) stimulation is desired.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth d2 that varies depending on the particular acupoint location. When stimulation is applied at the target tissue point, such stimulation is effective at treating a selected condition of the patient because there is something in the tissue at that location, or near that location, such as a nerve, a tendon, a muscle, or other type of tissue, that responds to the applied stimulation in a manner that contributes favorably to the treatment of the condition experienced by the patient.

FIG. 1B illustrates a sectional view of the IEAD 100 implanted so as to be centrally located under the skin at the selected target stimulation point 90, and over the acupoint axis line 92. Usually, for most patients, the IEAD 100 is implanted at a depth d1 of approximately 2-4 mm under the skin. The top (skin) side 102 of the IEAD is nearest to the skin 80 of the patient. The bottom (cathode) side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the target point 90 is located, the cathode 110 is also centered over the acupoint axis line 92.

FIG. 1B further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1B, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the target point location indicated on the skin.

As can be seen from FIG. 17, some acupoints may be located on the head of the patient, e.g., acupoints GV20, or in other tissue locations where the patient's skull bone, or other skeletal structure, prevent implanting the IEAD 100 very deep below the skin. This situation is illustrated schematically in FIGS. 17A and 17B. As seen in these figures, a bone 89, e.g., the skull bone, is right under the skin 80, with not much tissue separating the two. These two figures assume that the actual desired target stimulation point is a nerve 87 (or some other tissue formation) between the underneath side of the skin 80 and the top surface of the bone 89. Hence, the challenge is to implant the IEAD 100 in a manner that provides effective EA stimulation at the desired target stimulation site, e.g., at the nerve 87 (or other tissue formation) that resides beneath the acupoint 90. FIGS. 17A and 17B illustrate alternative methods for achieving this goal.

Shown in FIG. 17A is one alternative for implanting the IEAD 100 at an acupoint 90 located on the surface of the skin 80 above the bone 89, where the actual target stimulation point is a nerve 87, or some other tissue formation, that is located between the bone 89 and the underneath side of the skin 80. As shown in FIG. 17A, the IEAD 100 is implanted right under the skin with its front surface 106 facing down towards the target tissue location 87. This allows the electric fields (illustrated by the electric field gradient lines 88) generated by the IEAD 100 when EA stimulation pulses are to be generated to be most heavily concentrated at the target tissue stimulation site 87. These electric field gradient lines 88 are established between the two electrodes 110 and 120 of the IEAD. For the embodiment shown here, these two electrodes comprise a ring electrode 120, positioned around the perimeter edge of the IEAD housing, and a central electrode 110, positioned in the center of the front surface 102 of the IEAD housing. These gradient lines 88 are most concentrated right below the central electrode, which is where the target tissue location 87 resides. Hence, the magnitude of the electrical stimulation current will also be most concentrated at the target tissue location 87, which is the desired result.

FIG. 17B shows another alternative for implanting the IEAD 100 at the acupoint 90 located on the surface of the skin 80 above the bone 89, where the actual target stimulation point is a nerve 87, or some other tissue formation, that is located between the bone 89 and the underneath side of the skin 80. As shown in FIG. 17B, the IEAD 100 is implanted in a pocket 81 formed in the bone 89 at a location underneath the acupoint 90. In this instance, and as the elements are oriented in FIG. 17B, the front surface 106 of the IEAD 100 faces upwards towards the target tissue location 87. As with the implant configuration shown in FIG. 17A, this configuration also allows the electric fields (illustrated by the electric field gradient lines 88) that are generated by the IEAD 100 when EA stimulation pulses are generated to be most heavily concentrated at the target tissue stimulation site 87.

There are advantages and disadvantages associated with each of the two alternative implantation configurations shown in FIGS. 17A and 17B. Generally, the implantation procedure used to achieve the configuration shown in FIG. 17A is a simpler procedure with less risk. That is, all that need to be done by the surgeon to implant that EA device 100 as shown in FIG. 17A is to make an incision 82 in the skin 80 a short distance, e.g., 10-15 mm, away from the acupoint 90. This incision should be made parallel to the nerve 87 so as to minimize the risk of cutting the nerve 87. A slot is then formed at the incision by lifting the skin closest to the acupoint up at the incision and by carefully sliding the IEAD 100, with its front side 102 facing the skull, into the slot so that the center of the IEAD is located under the acupoint 90. Care is taken to assure that the nerve 87 resides below the front surface of the IEAD 100 as the IEAD is slid into position.

In contrast, if the implant configuration shown in FIG. 17B is to be used, then the implant procedure is somewhat more complicated with somewhat more risk. That is, to achieve the implant configuration shown in FIG. 17B, a sufficiently large incision must be made in the skin at the acupoint 90 to enable the skin 80 to be peeled or lifted away to expose the surface of the bone so that the cavity 81 may be formed in the bone. While doing this, care must be exercised to hold the nerve 87 (or other sensitive tissue areas) away from the cutting tools used to form the cavity 81. Once the cavity 81 is formed, the IEAD 100 is laid in the cavity, with its front surface 102 facing upward, the nerve 87 (and other sensitive tissue areas) are carefully repositioned above the IEAD 100, and the skin is sewn or clamped to allow the incision to heal. In this unique situation, where a cavity is formed in the bone to hold the IEAD 100, the back side 102 of the IEAD 100 (which sometimes is called the "skin" side), is actually farthest away from the skin surface.

However, while the surgical procedure and attendant risks may be more complicated when the configuration of FIG. 17B is employed, the final results of the configuration of FIG. 17B may be more aesthetically pleasing to the patient than are achieved with the configuration of FIG. 17A. That is, given the shallow space between the skin and the bone at an acupoint above the bone, the implant configuration of FIG. 17A will likely result in a small hump or bump at the implant site.

Insofar as Applicant is aware at the present time, of the two implant configurations shown in FIGS. 17A and 17B, there is no theoretical performance advantage that one implant configuration provides over the other. That is, both implant configurations should perform equally well insofar as providing EA stimulation pulses at the desired target tissue location 87 is concerned.

Thus, which implant configuration is used will, in large part, be dictated by individual differences in patient anatomy, patient preference, and surgeon preferences and skill levels.

From the above, it is seen that one of the main advantages of using a symmetrical electrode configuration that includes a centrally located electrode surrounded by an annular electrode, as is used in the embodiment described in connection with FIGS. 1-7, is that the precise orientation of the IEAD 100 within its implant location is not important. So long as one electrode faces and is centered over the desired target location, and the other electrode surrounds the first electrode (e.g., as an annular electrode), a strong electric field gradient is created that is aligned with the desired target tissue location. This causes the EA stimulation current to flow at (or very near to) the target tissue location 87.

FIG. 2 shows a plan view of the "cathode" (or "front") side 106 of the IEAD 100. As seen in FIG. 2, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2B, has a width W1 of about 1.0 mm, or approximately ½ of the width W2 of the IEAD.

FIG. 3 shows a plan view of the "back" (or "skin") side 102 of the IEAD 100. As will be evident from subsequent figure descriptions, e.g., FIGS. 5A and 5B, the back side 102 of the IEAD 100 comprises a cover plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the bottom case 124 in order to form the hermetically-sealed IEAD housing 100.

Figure 4:
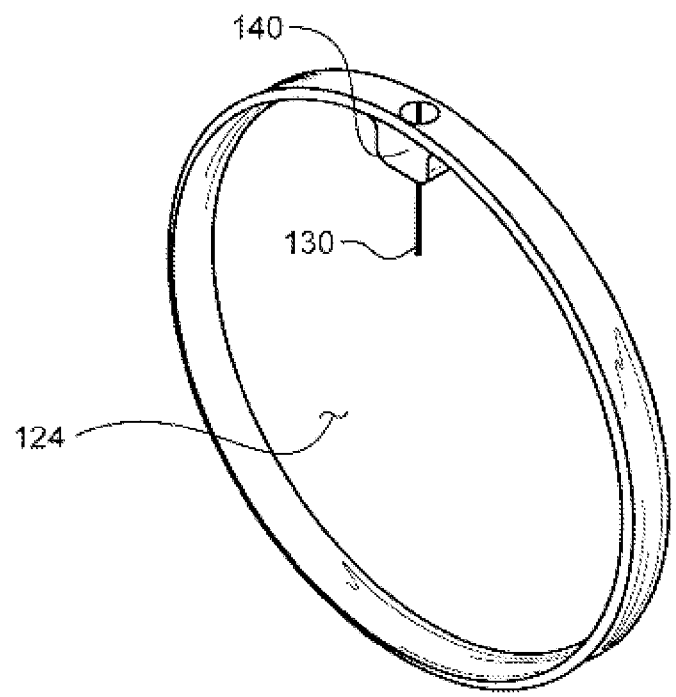
FIG. 4 is a perspective view of the IEAD housing, including a radial feed-through pin, before the electronic components are placed therein, and before being sealed with a cover plate.

FIG. 4 shows a perspective view of the IEAD case 124, including the feed-through pin 130, before the electronic components are placed therein, and before being sealed with the a cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
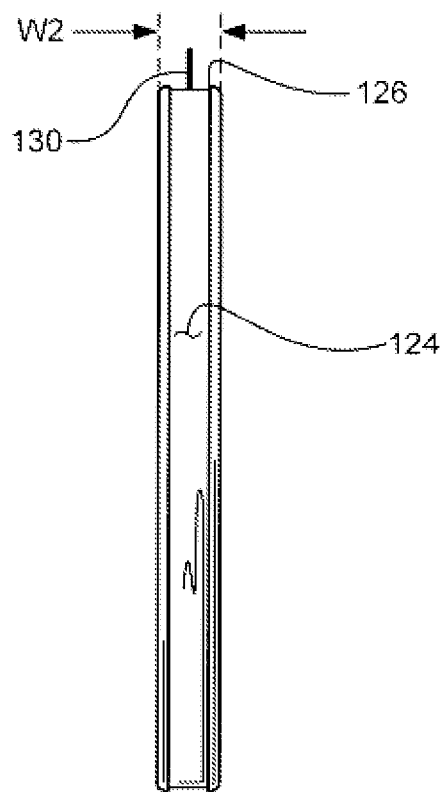
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm.) The diameter D4 is 0.80 mm with a tolerance of −0.06 mm. (Thus, with the tolerance considered, the diameter D4 could range from 0.74 mm to 0.80 mm.)

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Additional details associated with the radial feed-through pin 130, and its use within an electronic package, such as the IEAD 100 described herein, may be found in Applicant's co-pending U.S. patent application Ser. No. 13/777,901, filed Feb. 26, 2013, entitled "Radial Feed Through Packaging for an Implantable Electroacupuncture Device," which application was previously incorporated herein by reference.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the co-pending patent applications referenced above.

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a PC board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An over-molding process is used to accomplish this, although over-molding using silicone LSR 70 (curing temperature of 120° C.) with an injection molding process cannot be used. Over-molding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results.

FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single ring electrode 120. This is one of the preferred electrode configurations that has been described previously in connection, e.g., with the description of FIGS. 1-7, and is presented in FIG. 7A for reference and comparative purposes.

In the lower left corner of FIG. 7A, identified as "II", an electrode/array configuration is schematically illustrated that has a central electrode 310 of a first polarity surrounded by an oval-shaped electrode array 320a of two electrodes of a second polarity. (The oval-shaped electrode array 320a could also be other shapes, e.g., round.) When the two electrodes (of the same polarity) in the electrode array 320a are properly aligned with the body tissue being stimulated, e.g., aligned with a nerve underlying the desired acupoint, then such electrode configuration can stimulate the body tissue (e.g., the underlying nerve) at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a central electrode/array 310b of three electrode segments of a first polarity surrounded by an oval-shaped electrode array 320b of three electrode segments of a second polarity. (This oval-shaped array 320b could also be other shapes, e.g., round.) As shown in configuration III of FIG. 7A, the three electrode segments of the electrode array 320b are positioned more or less equidistant from each other, although a true equidistant positioning, especially relative to the central electrode array 310b, is not readily achieved with 3 electrodes placed in an oval-shaped array. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged symmetrically in a round or oval-shaped array. The four electrode segments of the electrode array 310c are likewise arranged symmetrically in a round or oval-shaped array. While preferred for many configurations, the use of a symmetrical electrode/array, whether as a central electrode array 310 or as a surrounding electrode/array 320, is not always required.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, ... n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

It should be noted that the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

For a more thorough description of the electrode materials best suited for the cathode electrode 110 and the anode electrode 120, as well as the surface area required for these electrodes, see Applicant's co-pending U.S. patent application Ser. No. 13/776,155, filed Feb. 25, 2013, "Electrode Configuration for an Implantable Electroacupuncture Device," previously incorporated hereby by reference.

Additional electrode configurations, both symmetrical electrode configurations and non-symmetrical electrode configurations, that may be used with an EA stimulation device as described herein, are illustrated in Appendix A and Appendix B.

Electrical Design

Next, with reference to FIGS. 8A-16, the electrical design and operation of the circuits employed within the IEAD 100 will be described. Additional details regarding the electrical design and operation of the IEAD may be gleaned from Applicant's co-pending U.S. patent application Ser. No. 13/769,699, filed Feb. 18, 2013, entitled "Circuits and Methods for Using a High Impedance, Thin, Coin-cell Type Battery in an Implantable Electroacupuncture Device," which application is incorporated herein by reference.

Figure 8A:
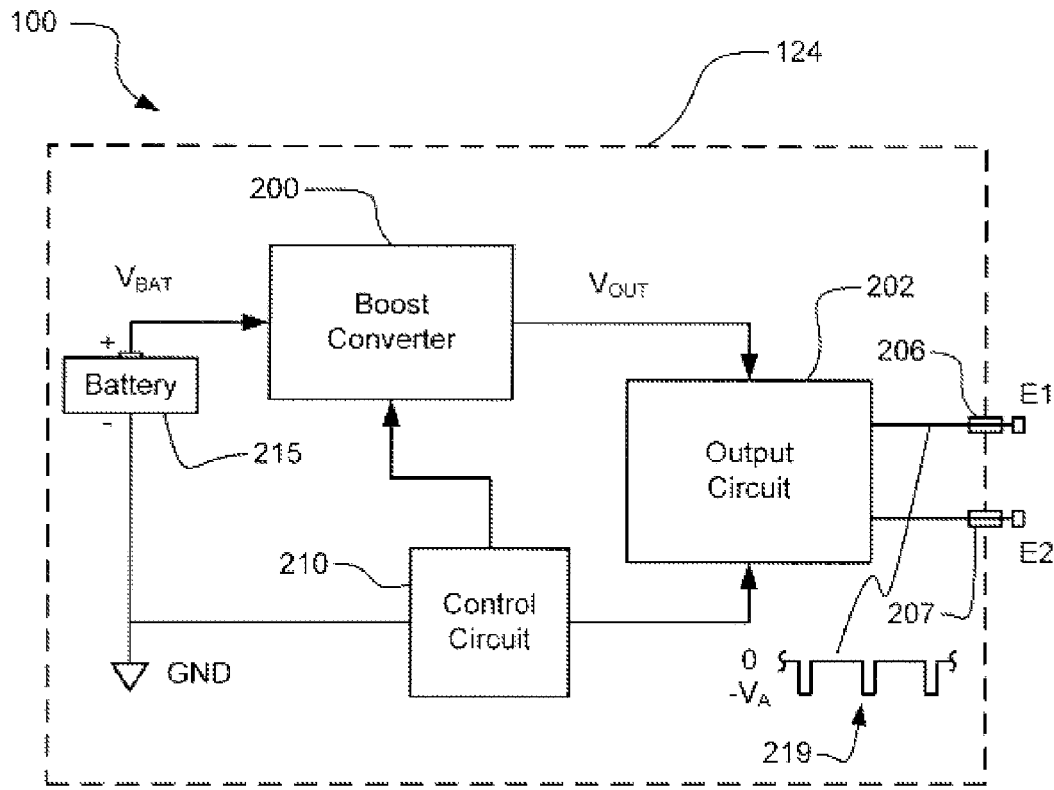
FIG. 8A illustrates a functional block diagram of the electronic circuits used within an IEAD of the type disclosed herein.

FIG. 8A shows a functional block diagram of an implantable electroacupuncture device (IEAD) 100 made in accordance with the teachings disclosed herein. As seen in FIG. 8A, the IEAD 100 uses an implantable battery 215 having a battery voltage $V_{BAT}$. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

As explained more fully below in connection with the description of FIGS. 15A and 15B, and as can also be seen from the waveform 219 shown in the lower right corner of FIG. 8A, the prescribed stimulation regimen typically comprises a continuous stream of stimulation pulses having a fixed amplitude, e.g., $V_A$ volts (also referred to as an amplitude A1), a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week. Other stimulation regimens may also be used, e.g., using a variable frequency for the stimulus pulse during a stimulation session rather than a fixed frequency. Also, the rate of occurrence of the stimulation session may be varied from as short as, e.g., 1 day, to as long as, e.g., 14 days.

The electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny battery inside of the coin-sized stimulator provides enough energy for the stimulator to carry out its specified stimulation regimen over a period of several years. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
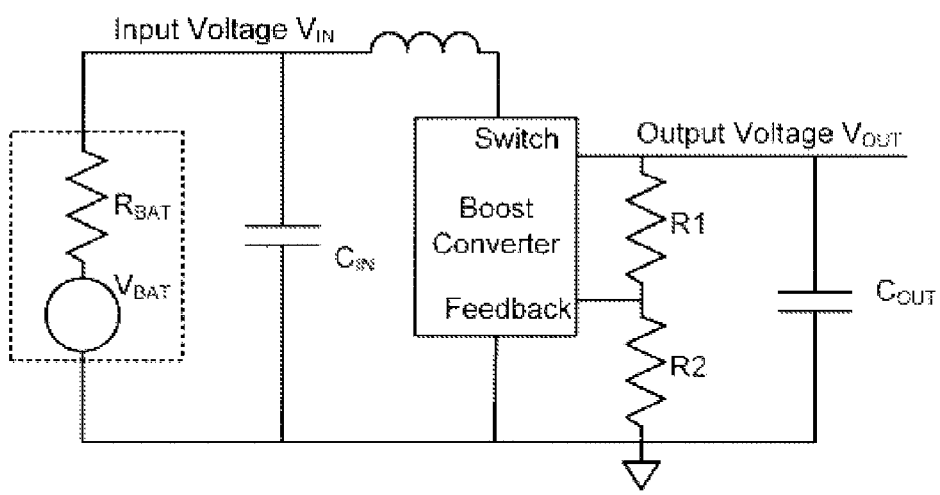
FIG. 8B shows a functional block diagram of a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electroacupuncture device.

In the boost converter circuit example shown in FIG. 8B, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
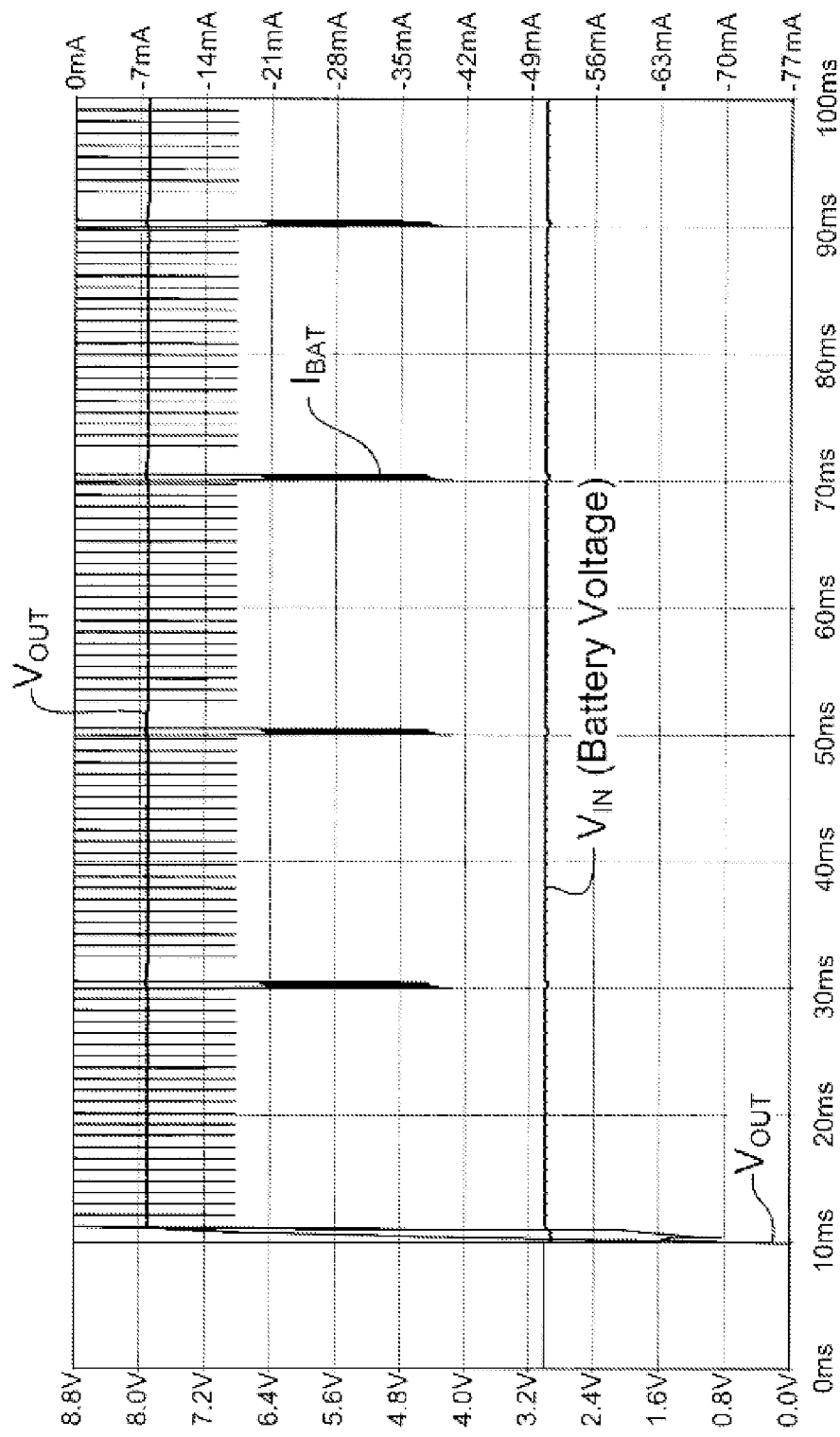
FIG. 9A illustrates a typical voltage and current waveform for the circuits of FIGS. 8A and 8B when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
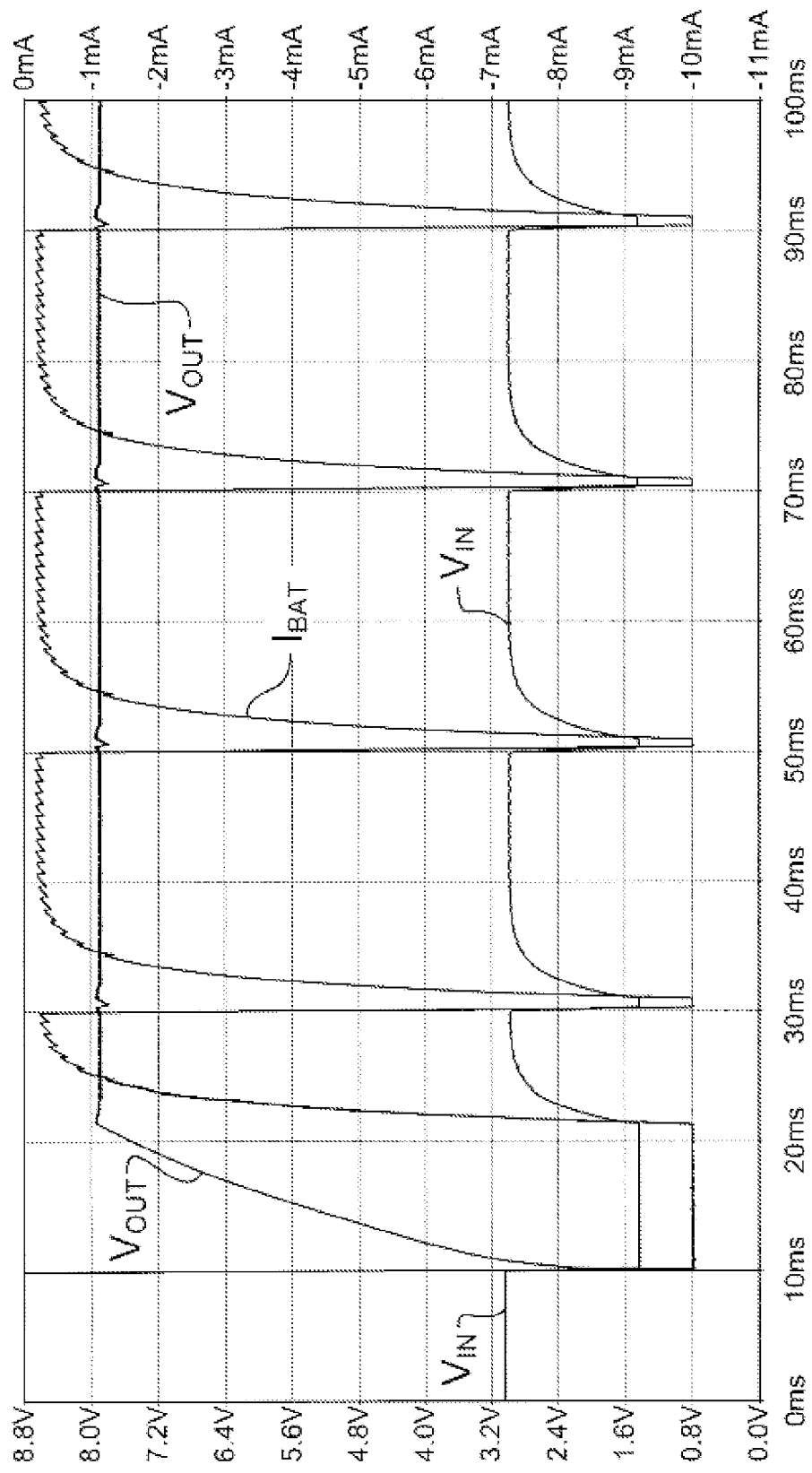
FIG. 9B shows the voltage and current waveforms for the circuits of FIGS. 8A and 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electro-acupuncture stimulus pulses. The resulting drops in output voltage $V_{OUT}$ are not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when EA stimulation pulses are generated.

Figure 10:
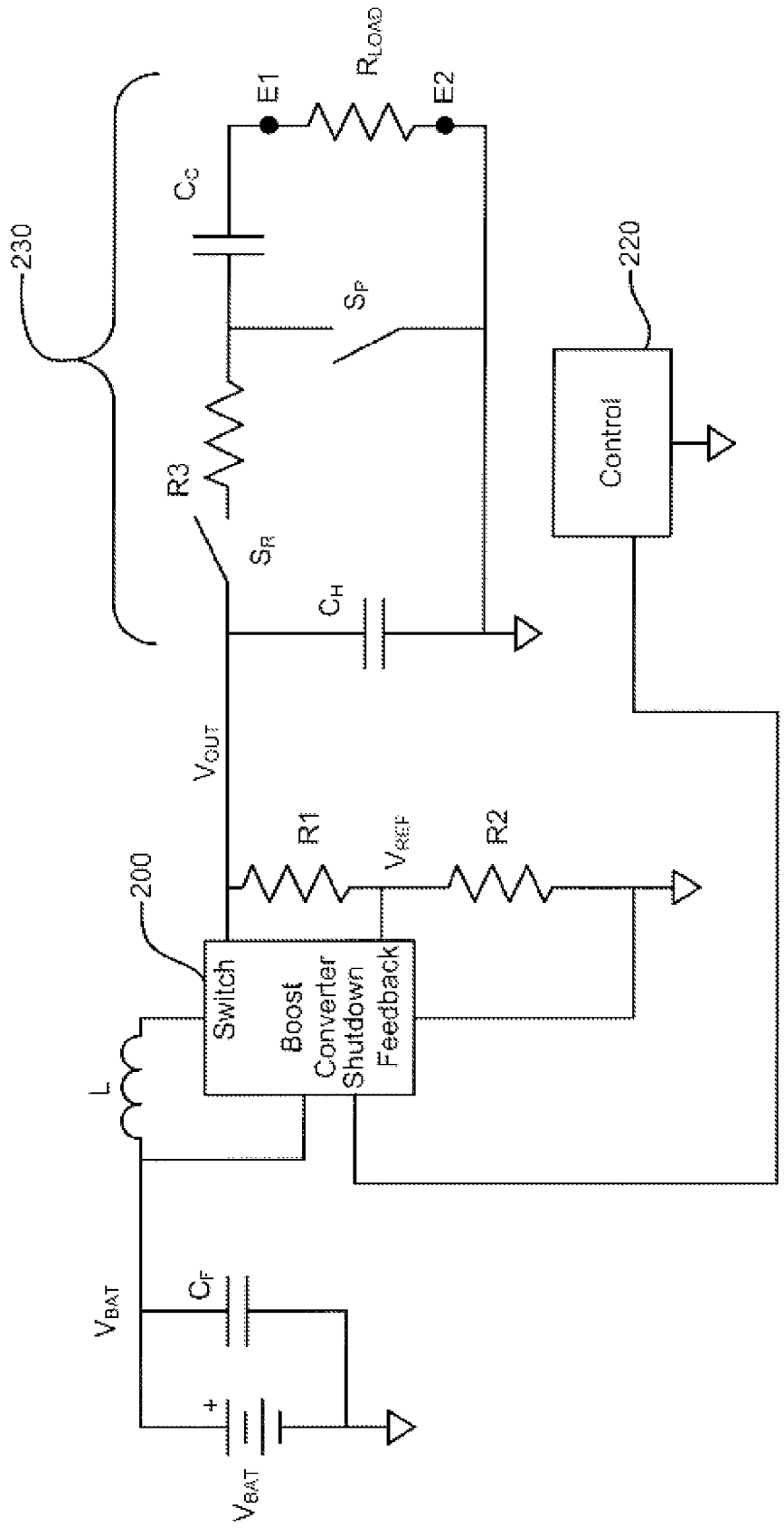
FIG. 10 shows a functional diagram of one preferred boost converter circuit and pulse generation circuit for use within the IEAD.

To provide this needed current management, the IEAD 100 disclosed herein employs electronic circuitry as shown in FIG. 10, or equivalents thereof. Similar to what is shown in FIG. 8A, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and Sp are kept open, with a voltage approximately equal to the output voltage $V_{OUT}$ appearing across the coupling capacitor $C_C$.

At the leading edge of a stimulus pulse, the switch Sp is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor $C_F$ is recharged from the battery during the relatively long OFF time when the control signal disables the boost converter circuit.

Figure 11:
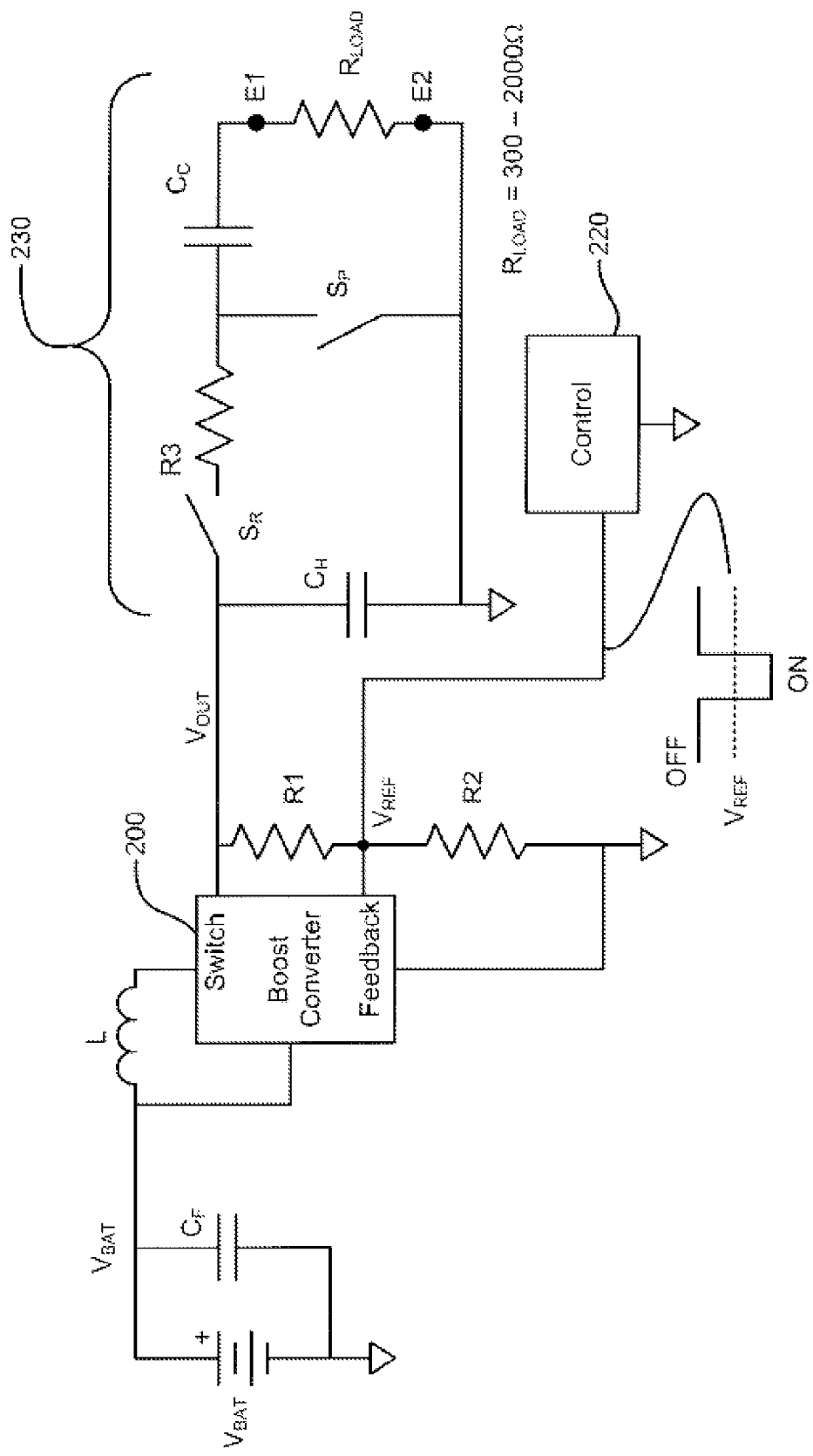
FIG. 11 shows an alternate functional diagram of a boost converter circuit and pulse generation circuit for use within the IEAD.

An alternate embodiment of the electronic circuitry that may be used within the IEAD 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
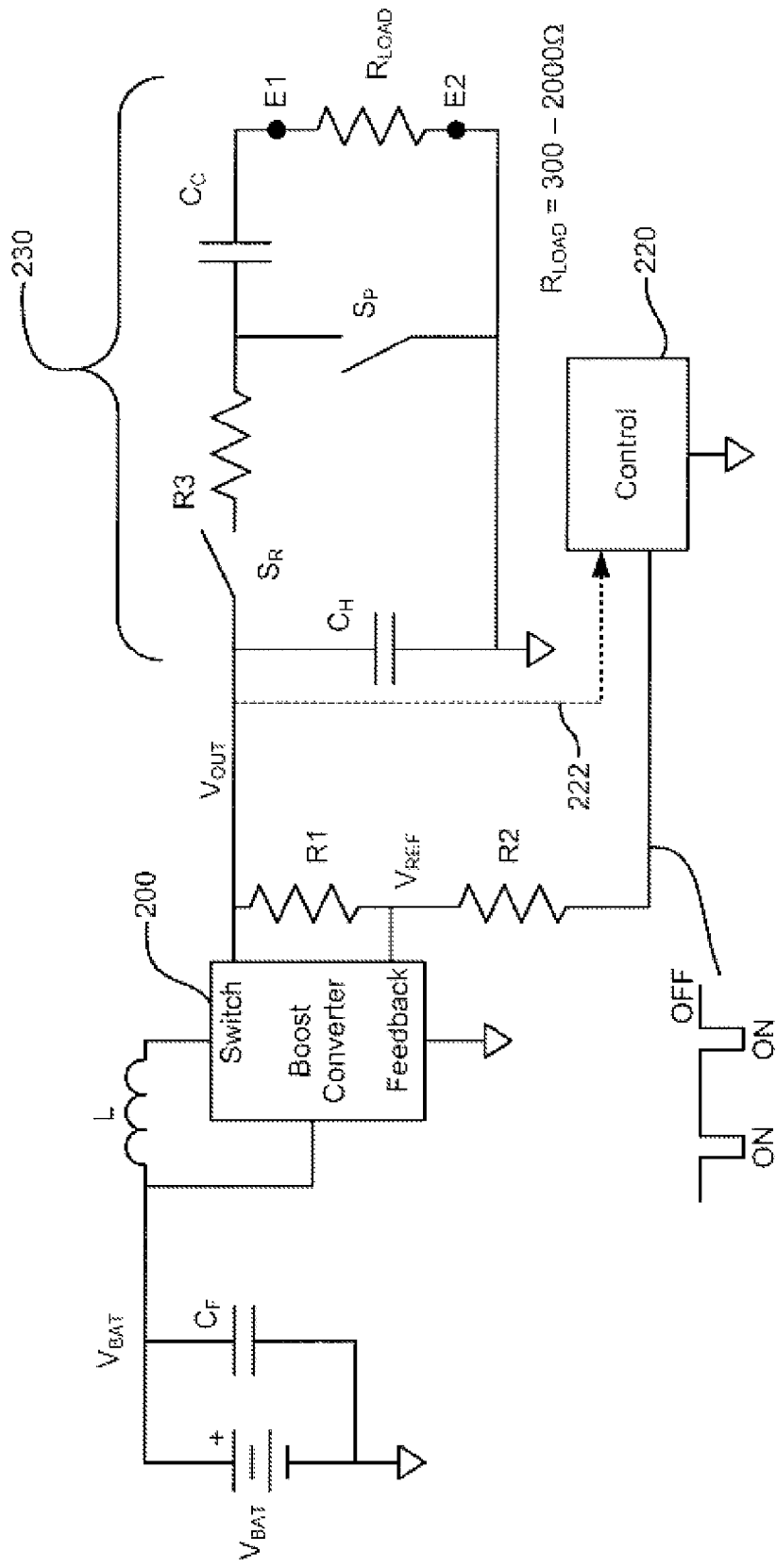
FIG. 12 shows a refinement of the functional circuit configurations of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
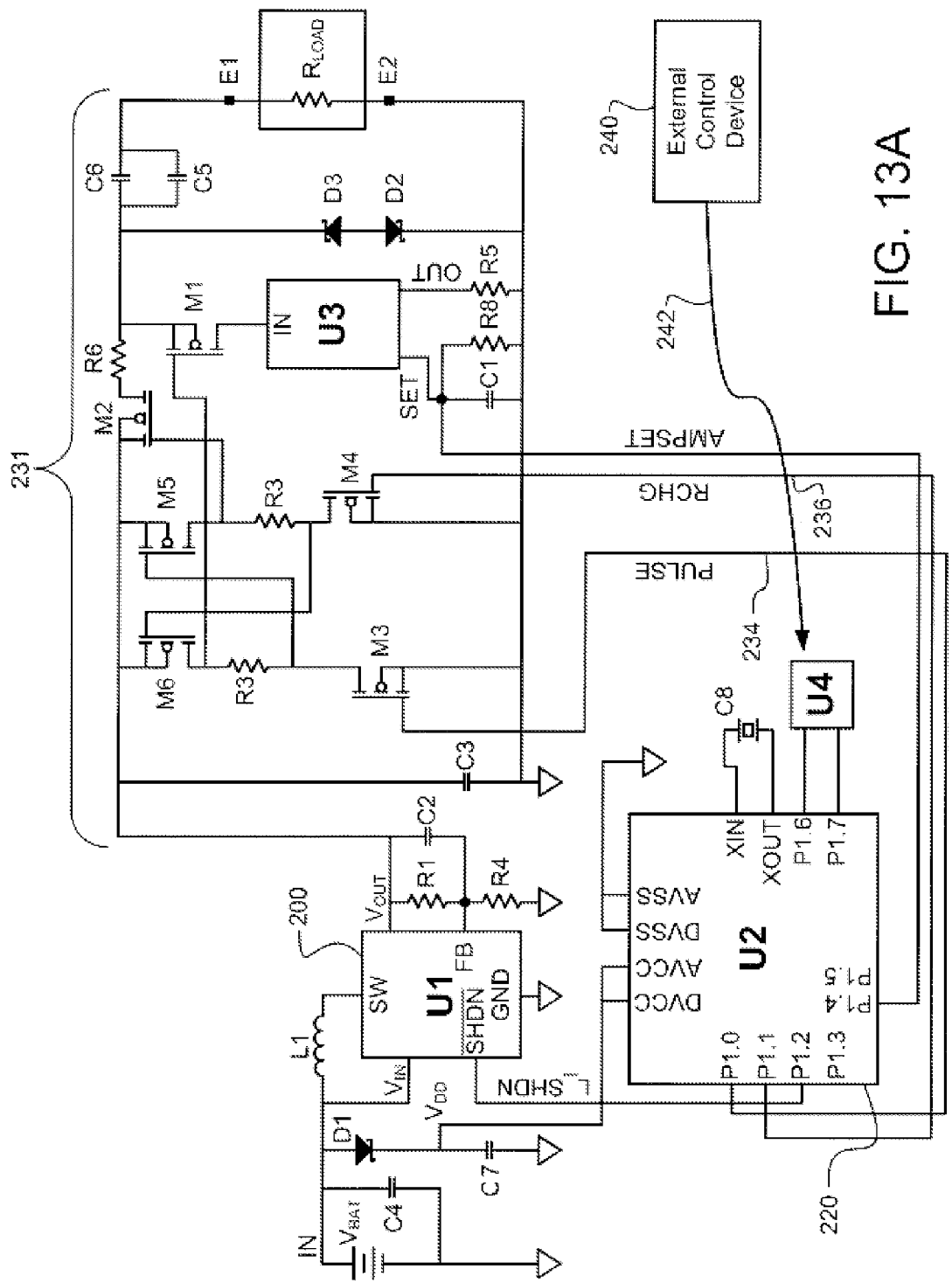
FIG. 13A shows one preferred schematic configuration for use within an IEAD that implements the functional circuits shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G2452I micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIGS. 10, 11, 12, 13A, or equivalents thereof, have some means for controlling the stimulation current that flows through the load, $R_{LOAD}$, which load may be characterized as the patient's tissue impedance at and around the acupoint being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 13A by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
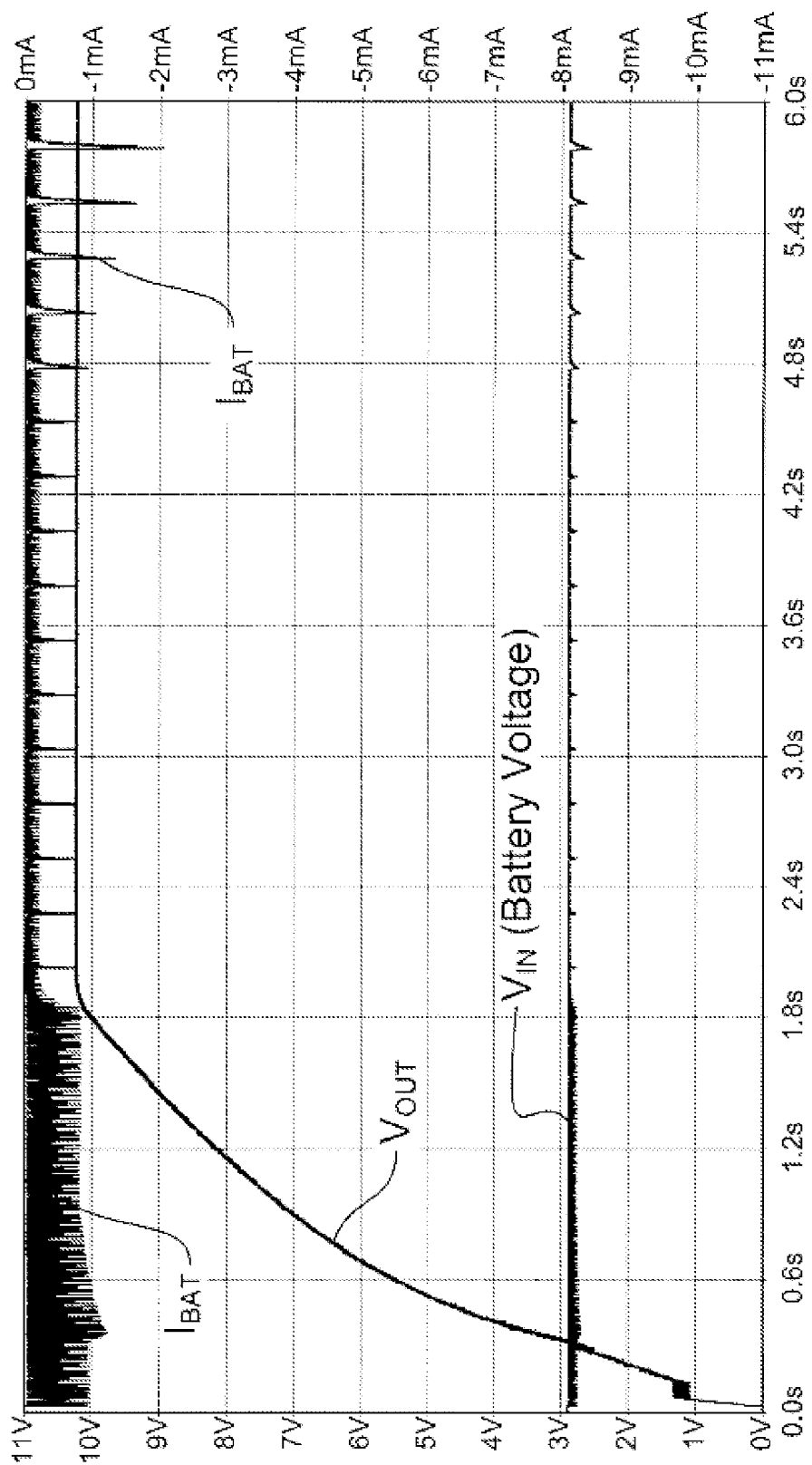
FIG. 13B shows current and voltage waveforms associated with the operation of the circuits shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13A have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
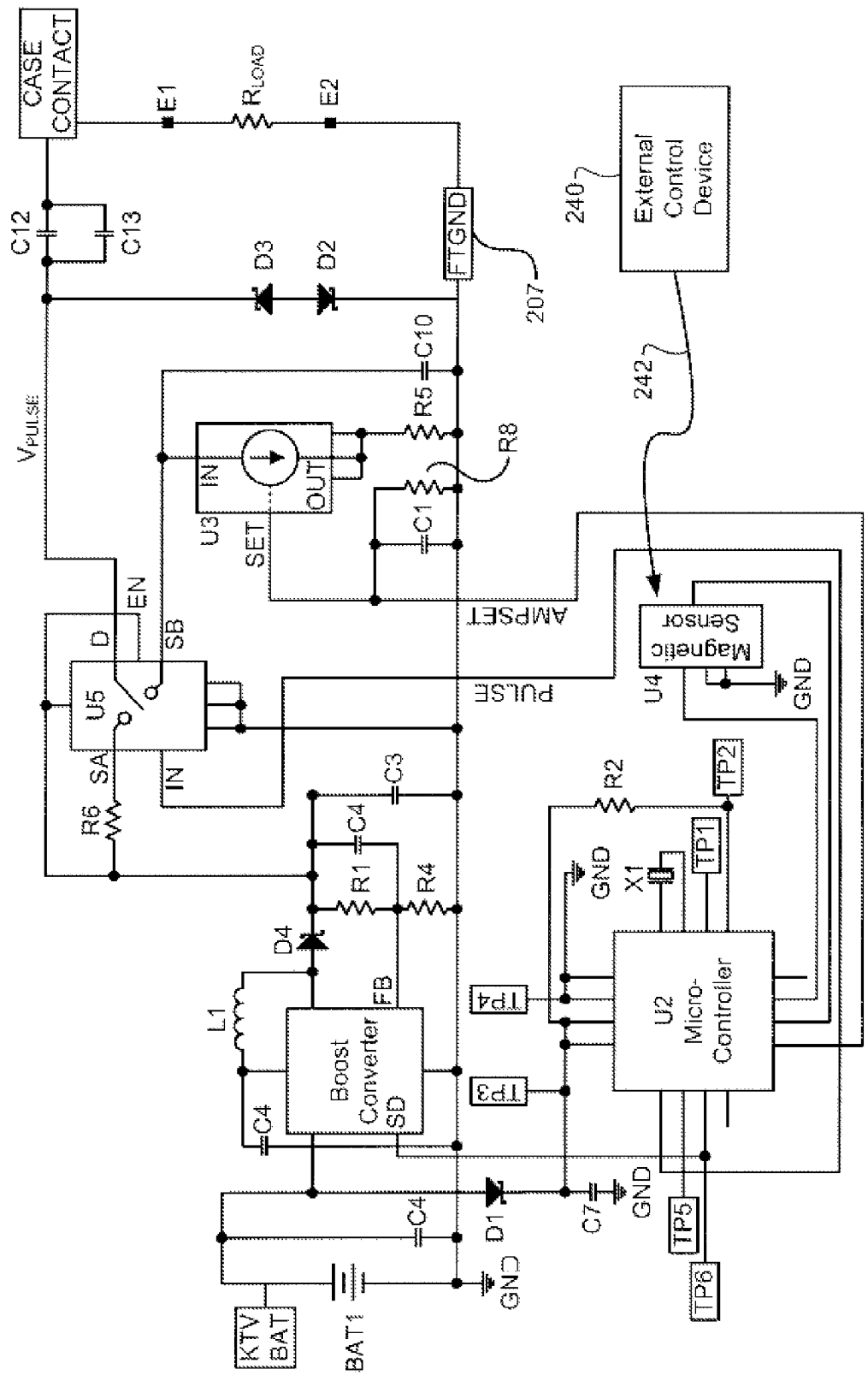
FIG. 14 illustrates another preferred schematic configuration for an IEAD similar to that shown in FIG. 13A, but which uses an alternate output circuitry configuration for generating the stimulus pulses.

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of a Schottky diode D4 at the output terminal of the boost convertor U1 and the inclusion of a fifth integrated circuit (IC) U5 that essentially performs the same function as the switches M1-M6 shown in FIG. 13A.

The Schottky diode D4 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (electromagnetic sensor) are basically the same as the IC's U1, U2, U3 and U4 described previously in connection with FIG. 13A.

The IC U5 shown in FIG. 14 functions as a single pole/double throw (SPDT) switch. Numerous commercially available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

Figure 14A:
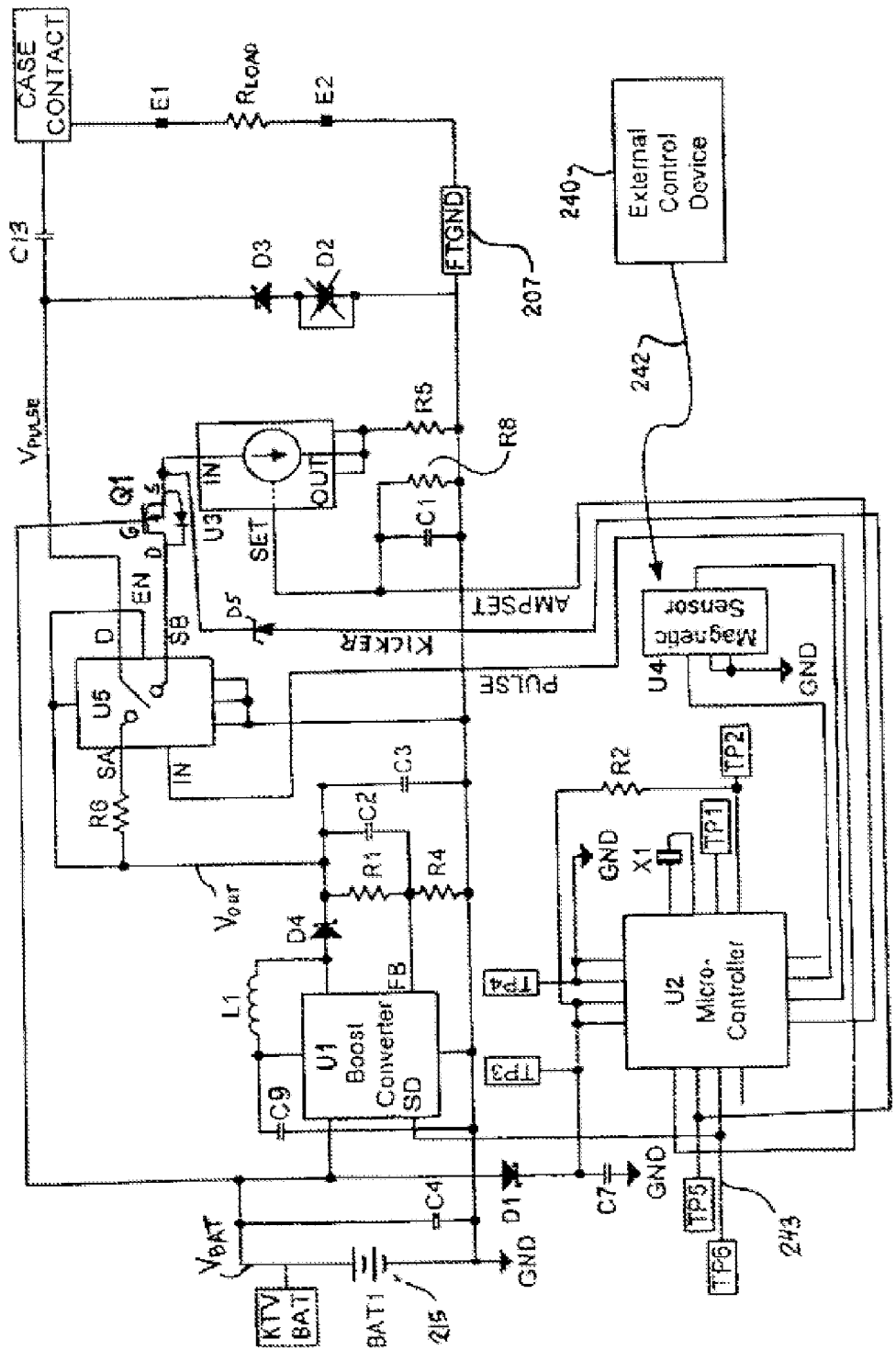
FIG. 14A depicts yet a further preferred schematic configuration for an IEAD similar to that shown in FIG. 13A or FIG. 14, but which includes additional enhancements and circuit features.

Yet another preferred embodiment of the circuitry used in an implantable electroacupuncture device (IEAD) 100 that employs an ON-OFF approach to duty-cycle modulate the boost converter as a tool for limiting the amount of instantaneous battery current drawn from the high impedance battery 215 is shown in the schematic diagram of FIG. 14A. The circuit shown in FIG. 14A is, in most respects, very similar to, or the same as, the circuit described previously in connection with FIG. 14 or FIG. 13A, and that description will not be repeated here. What is new in FIG. 14A are the addition of elements and features that address additional issues associated with the operation of an IEAD 100.

One feature included in the circuitry of FIG. 14A, which is described briefly above in connection with the description of FIG. 10, is that the boost converter circuit U1 is modulated ON and OFF using digital control generated within the boost converter circuit U1 itself. In accordance with this variation, the boost converter circuit 200 shuts itself down whenever the battery voltage falls below a predetermined level above that required by the remaining circuitry. For example, in the embodiment shown in FIG. 14A, the boost converter circuit U1 is realized using a MAX8570 boost converter IC, commercially available from Maxim, or equivalents thereof. This particular boost converter IC shuts down when the applied voltage, $V_{BAT}$, falls below 2.5 V. Advantageously, a battery voltage of 2.5 volts is still high enough to ensure the microcontroller IC U2, and other circuitry associated with the operation of the IEAD 100, remain operational.

Thus, in operation, as soon as the battery voltage drops below 2.5 volts, the boost converter circuit U1 shuts down, thereby limiting the instantaneous current drawn from the battery. When the boost converter U1 shuts down, the instantaneous battery current drawn from the battery is immediately reduced a significant amount, thereby causing the battery voltage $V_{BAT}$ to increase.

As the battery voltage $V_{BAT}$ increases, the boost converter circuit U1 remains shut down until the microcontroller U2 determines that it is time to turn the boost converter back ON. This turn ON typically occurs in one of two ways: (1) just prior to the delivery of the next stimulus pulse, a turn ON signal may be applied to the Shutdown ("SD") terminal, signal line 243, of the boost converter circuit U1; or (2) as soon as the battery voltage, $V_{BAT}$, has increased a sufficient amount, as sensed at the feedback terminal FB of the boost converter circuit U1, the circuits within the boost converter circuit U1 are automatically turned back ON, allowing the output voltage $V_{OUT}$ to build up to a voltage level needed by the switch circuit U5 and the current source circuit U3 to generate an output stimulus pulse of the desired amplitude when the next PULSE signal is applied to the IN terminal of the switch U5 by the microcontroller U2.

Once turned ON, the boost converter remains ON until, again, the input voltage drops below 2.5 volts. This pattern continues, with the boost converter being ON for a short time, and OFF for a much longer time (typically, the duty cycle associated with this ON/OFF operation of the boost converter circuit U1 is no greater than about 0.01), thereby controlling and limiting the amount of current that is drawn from the battery. This ON/OFF action of U1 assures that the battery voltage, $V_{BAT}$, always remains sufficiently high to permit operation of all the critical circuits of the IEAD 100 (principally the circuits of the microcontroller U2), except the boost converter circuit U1.

In a preferred implementation, the microcontroller circuit U2 used in FIG. 14A comprises an MSP430G2452IRSA 16 micro-controller, commercially available from Texas Instruments, or equivalent microcontroller The current source circuit U3 comprises a LT3092 programmable current source commercially available form Linear Technology, or equivalents thereof. The sensor circuit U4 comprises an AS-M15SA-R magnetic sensor, commercially available from Murata, or equivalents thereof. And, the switch circuit U5 comprises an ADG1419BCPZ single pole double throw analog switch commercially available from Analog Devices, or equivalents thereof.

Another feature or enhancement provided by the circuit implementation depicted in FIG. 14A relates to removing, or at least minimizing, some undesirable leading edge transients that are seen in the output stimulus pulses generated by the circuitry of FIG. 14. The solution to remove or mitigate the occurrence of such leading edge transients is to insert an N-MOSFET transistor switch Q1 at the input terminal, IN, of the programmable current source circuit U3. This switch Q1 acts as a "cascode" stage that maintains a more constant voltage across the current source U3 as the output current and/or load resistance changes. The gate (G) terminal of the switch Q1 is driven by the battery voltage, $V_{BAT}$, which means the voltage at the source terminal (S) of switch Q1, which is connected to the IN terminal of the current source U3, is limited to roughly $V_{BAT}-V_{Gs}$, where $V_{is}$ is the threshold voltage across the gate (G)-source (S) terminals of Q1.

Use of this N-MOSFET switch Q1 as depicted in FIG. 14A advantageously reduces the transient leading edge of the stimulus pulse because the capacitance looking into Q1 is much less than is seen when looking into the current source circuit U3 because of the Miller effect. That is, there is considerable loop gain in the operation of the U3 current source circuit to servo the current. This loop gain directly scales the input capacitance so that there is a much larger leading edge spike on the pulse. This in turn causes a 30 to 40 microsecond transient at the leading edge of the current pulse as the current source U3 recovers current regulation.

Figure 14B:
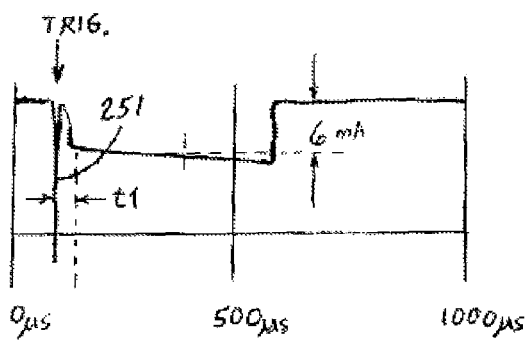
FIGS. 14B and 14C show timing waveform diagrams that illustrate the operation of the circuit of FIG. 14 before (FIG. 14B) and after (FIG. 14C) the addition of a cascode stage to the IEAD circuitry that removes some undesirable transients from the leading edge of the stimulus pulse.

An example of this leading edge transient is illustrated in the timing waveform diagram of FIG. 14B. In FIG. 14B (as well as in FIGS. 14C, 14D and 14E, which all show similar timing waveform diagrams), the horizontal axis is time and the vertical axis is voltage, which (assuming a resistive load of 600 ohms) may readily be converted to current, as has been done in these figures. The stimulus pulse begins at a trigger location near the left edge of the waveform, labeled TRIG. As seen in FIG. 14B, immediately after the trigger point, which should mark the beginning or leading edge of the stimulus pulse, an initial spike 251 occurs that has a magnitude on the order of twice the amplitude of the stimulus pulse. This spike 251 shoots down (as the waveform is oriented in the figures) and then shoots back up, and eventually, after a delay of t1 microseconds, becomes the leading edge of the pulse. The delay t1 is about 30-40 microseconds, which means that the leading edge of the stimulus pulse is delayed 30-40 microseconds. Having a leading edge delay of this magnitude is not a desirable result.

Figure 14C:
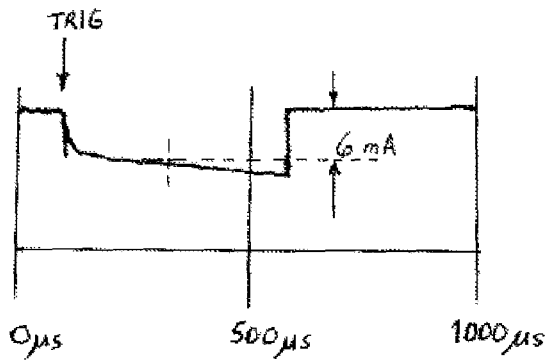

Next, with the cascode stage (comprising the switch Q1) connected to the input terminal, IN, of the current source U3, the stimulus pulse is again illustrated. Because the cascode stage significantly reduces the input capacitance looking into the drain (D) terminal of the switch Q1, the leading edge transient is significantly reduced, as illustrated in the timing waveform diagram of FIG. 14C. As seen in FIG. 14C, the leading edge transient has all but disappeared, and the delay t1 between the trigger point and the leading edge of the stimulus pulse is negligible.

Figure 14D:
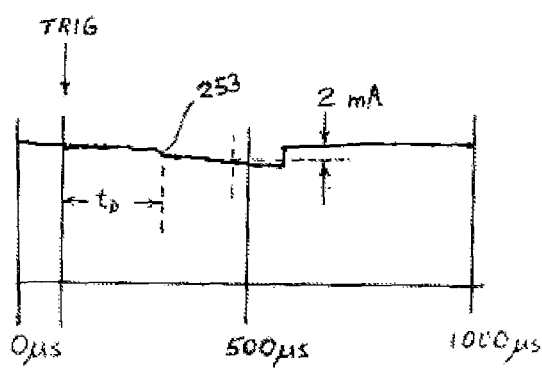
FIGS. 14D and 14E illustrate timing waveform diagrams that show the operation of the circuit of FIG. 14 before (FIG. 14D) and after (FIG. 14E) the addition of circuitry that addresses a delay when starting the current regulator U3 for low amplitude stimulus pulses.

Another feature or enhancement provided by the circuitry of FIG. 14A is to address a delay that is seen when starting up the programmable current source U3 at low pulse amplitudes, (e.g., less than about 3 mA). A typical current stimulus output for the IEAD is on the order of 15-25 mA. When a much smaller amplitude current stimulus is used, e.g., 1.5-3 mA, the control signal that defines this smaller amplitude pulse is significantly less than the one used to define the more typical stimulus amplitudes of 15-25 mA. Such a small control signal lengthens the delay, $t_D$, between the trigger point, TRIG, and the leading edge 253 of the stimulus pulse. FIG. 14D illustrates this long delay, $t_D$, which is on the order of 200 microseconds.

The address the problem illustrated in the waveform diagram of FIG. 14D, a Schottky diode D5 is connected in the circuit of FIG. 14A from an output port on the microcontroller circuit U2 to the input port, IN, of the current source circuit U3. In a preferred implementation of the circuit of FIG. 14A, this Schottky diode D5 is realized using a BAT54XV2DKR diode, commercially available from Fairchild Semiconductor. This diode is used to warm-up or "kick start" the circuit U3 when the pulse amplitude is low so that there is less of a delay, $t_D$, before current is regulated at the start of the pulse. Since the cascode stage Q1 keeps the drop across U3 low, U3 can be driven directly from the microcontroller U2 at the start of the pulse without significantly changing the pulse characteristics (e.g., amplitude or timing) in such a way that the delay, $t_D$, before current is regulated at the start of the pulse can be reduced.

Figure 14E:
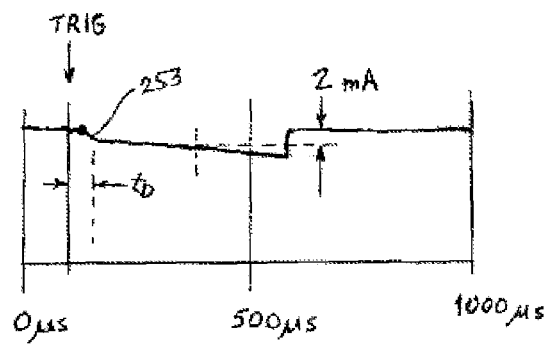

FIG. 14E illustrates the timing waveform diagram achieved using the circuit of FIG. 14A with the diode D5 inserted so as to allow the microcontroller U2 to directly drive, or "kick start", the current source circuit U3 at the start of the pulse. As seen in FIG. 14E, the delay, $t_D$, realized with the "kick start" has been significantly reduced from what it was without the "kick start" (as shown in FIG. 14D), e.g., from about 200 microseconds to about 40 microseconds, or less. Thus, this "kick start" feature shortens the undesired delay, $t_D$, by at least a factor of about 5.

An additional feature provided by the circuitry of FIG. 14A addresses a concern regarding EMI (electromagnetic interference). EMI can occur, for example, during electrocautery and/or external defibrillation. Should any of the circuit elements used within the IEAD 100, such as the analog switch U5, have a transient voltage exceeding approximately 0.3 V appear on its pins (which transient voltage could easily occur if the IEAD is subjected to uncontrolled EMI), then the IC could be damaged. To prevent such possible EMI damage, the output voltage pulse, appearing on the signal line labeled $V_{PULSE}$, is clamped to ground through the forward bias direction of the diode D3. In contrast, in the circuits shown in FIGS. 13A and 14, there are two zenor diodes, D2 and D3, connected back to back, to limit the voltage appearing on the $V_{PULSE}$ line to voltages no greater than the zenor diode voltage in either direction. As seen in FIG. 14A, diode D2 has been replaced with a short, thereby clamping the voltage that can appear on the output voltage line—the signal line where $V_{PULSE}$ appears—in one polarity direction to no greater than the forward voltage drop across the diode D3.

Figure 15:
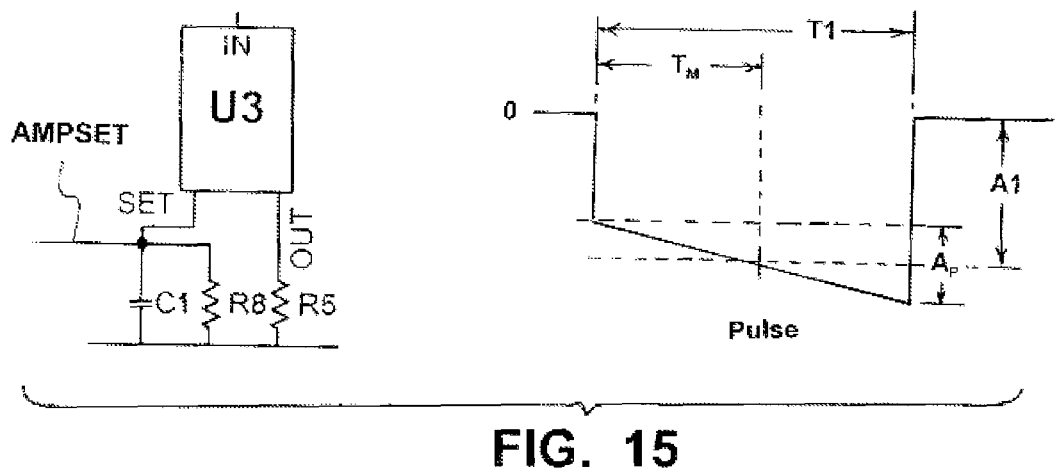
FIG. 15 shows a reverse trapezoidal waveform of the type that is generated by the pulse generation circuitry of the IEAD, and further illustrates one approach for achieving the desired reverse trapezoidal waveform shape.
Figure 15A:
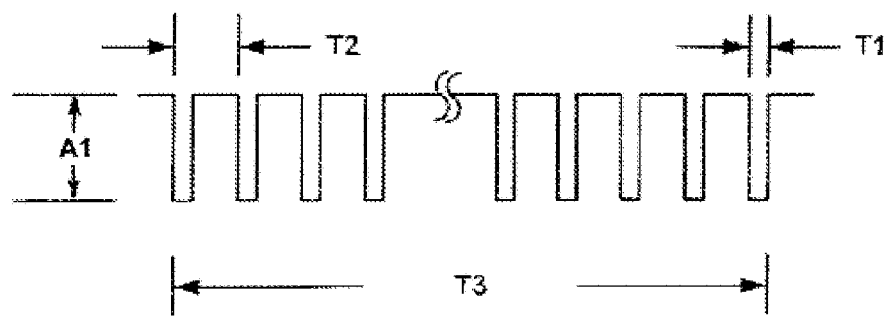
FIG. 15A shows a timing waveform diagram of representative EA stimulation pulses generated by the IEAD during a stimulation session in accordance with a specified stimulation regimen.

As is evident from the waveforms depicted in FIGS. 14B, 140, 14D and 14E, the basic current stimulus waveform is not a square wave, with a "flat top", (or, in the case of a negative current waveform, with a "flat bottom") as depicted in most simplified waveform diagrams (see, e.g., FIG. 15A). Rather, the current stimulus waveforms shown in FIGS. 14B, 140, 14D and 14E have what the inventors refer to as a reverse trapezoidal shape. That is, the current waveforms start at a first value, at the leading edge of the pulse, and gradually ramp to a second, larger, value at the trailing edge of the pulse (i.e., the current increases during the pulse). For a negative-going pulse, as is shown in these figures, the ramp slopes downward, but this corresponds to the amplitude of the pulse getting larger.

This pulse shape—a reverse trapezoidal shape—for the current stimulus pulse is by design. That is, the inventors want the current to increase during the pulse because such shape is believed to be more selective for the recruitment of smaller fiber diameter tissue and nerves, and thus has the potential to be more effective in achieving its intended goal of activating desired tissue at the target tissue location.

The reverse trapezoidal stimulus pulse shape is illustrated in more detail in FIG. 15, as is one manner for achieving it. Shown on the right side of FIG. 15 is a sketch of reverse trapezoidal pulse. (Note, it is referred to as a "reverse trapezoidal" pulse because the current, or waveform, gets larger or increases during the pulse. This is in contrast to a conventional voltage regulated pulse, which is "trapezoidal", but in the other direction, i.e., the current decreases during the pulse.) As seen in FIG. 15, the reverse trapezoidal pulse has a duration T1, but the magnitude (amplitude) of the current during the pulse increases from a first value at the leading edge of the pulse to a second value at the trailing edge of the pulse. The increase in current from the leading edge of the pulse to the trailing edge is a value $A_P$. The average amplitude of the pulse during the pulse time T1 is a value A1, which is typically measured at a time $T_M$, which is about in the middle of the pulse. That is, $T_M=\frac{1}{2}T1$.

Also shown in FIG. 15, on the left side, is the circuitry that is used to create the reverse trapezoidal waveform. This circuitry is part of the circuitry shown, e.g., in FIG. 14A, and includes a capacitor C1 in parallel with a large resistor R8 (270 KΩ) connected to the "set" terminal of the programmable current source U3. The "AMPSET" signal, generated by the micro-controller circuit U2 to set the amplitude A1 of the current stimulus pulse to be generated, is applied to the "set" terminal of U3. When enabled by the AMPSET signal, the capacitor C1 starts to charge up during the pulse at a rate of approximately 10 µA (which comes from the "set" pin of U3, i.e., from the circuitry inside of U3). For C1=0.1 microfarads, this turns out to be 100 mV/ms, or 50 mV for a pulse having a pulse duration or width (T1) of 0.5 ms. Since the pulse current is approximately equal to $V_{SET}/R5$, the pulse current will increase by 50 mV/R5. Or, where R5 is 22 ohms, this increase in current turns out to be 50 mV/22=2.27 mA at the end of the 0.5 ms pulse. This increase is essentially fixed regardless of the programmed pulse amplitude.

While the circuitry described above performs the intended function of causing the current stimulus pulse to have a reverse trapezoidal shape in a simple and straightforward manner, it should be noted that there are other circuits and techniques that could also be used to achieve this same result. Moreover, it would be possible to directly control the shape of the $V_{SET}$ signal during the pulse duration in order to create any desired stimulus pulse shape.

As shown in embodiment of the IEAD shown in FIG. 14A, the stimulation circuitry uses a micro-controller integrated circuit (IC) U2 which generates all of the operating control signals needed to guide other circuits, including the Boost Converter circuit IC U1, to generate the desired stream of stimulation pulses. These other circuits include a programmable current source IC U3, an analog switch U5, and a magnetic sensor U4. As can be seen in FIG. 14A, the micro-controller circuit U2 is driven by a clock circuit that includes a crystal oscillator to provide a very stable frequency reference. However, when the stimulus pulses are not being generated—which is most of the time given the very low duty cycle of operation, e.g., T3/T4 is less than 0.05—the micro-controller U2 is able to go into a very low power sleep state, thereby conserving power.

In order for the present invention to provide accurate chronotherapeutics (i.e., the delivery of stimulation sessions having very precise stimulation parameters at very precise times), it would be desirable to use a crystal time base. In the existing micro-controller U2 design, however, the crystal clock circuit does not provide an accurate time base; rather, all it provides is a steady or stable clock signal that can be counted using simple counter circuits. A crystal time base, on the other hand, could accurately perform all the functions of a rather sophisticated stop watch, including keeping track of multiple time bases.

A crystal time base (operating all the time—which it would need to do to provide accurate chronotherapeutics) would roughly double the battery current between therapy sessions, thereby taking the nominal longevity of the implantable electroacupuncture device (IEAD) down roughly from 3 years to 2 years.

Reducing the longevity of the IEAD by a factor of ⅓ is not viewed as an acceptable tradeoff to provide accurate chronotherapeutics. Hence, what is needed is a design, or alternate approach, whereby an accurate time base could be provided without sacrificing a significant loss in longevity of the IEAD.

One way to accomplish this desired result is to add another small IC to the circuits of the IEAD that functions as a real time clock (RTC). Such RTC may be realized from a very small device (3.2×1.5 mm) that runs on 360 nanoAmps (nA) of current. Such device, referred to as a Real Time Clock Module is commercially available from Micro Crystal AG, of Grenchen, Switzerland, as part number RV-4162-C7.

Figure 15B:
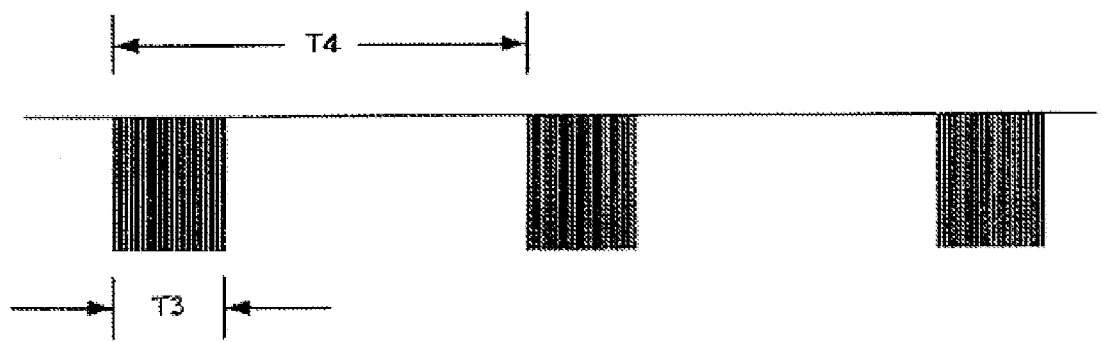
FIG. 15B shows a timing waveform diagram of multiple stimulation sessions, and illustrates the waveforms on a more condensed time scale.
Figure 15C:
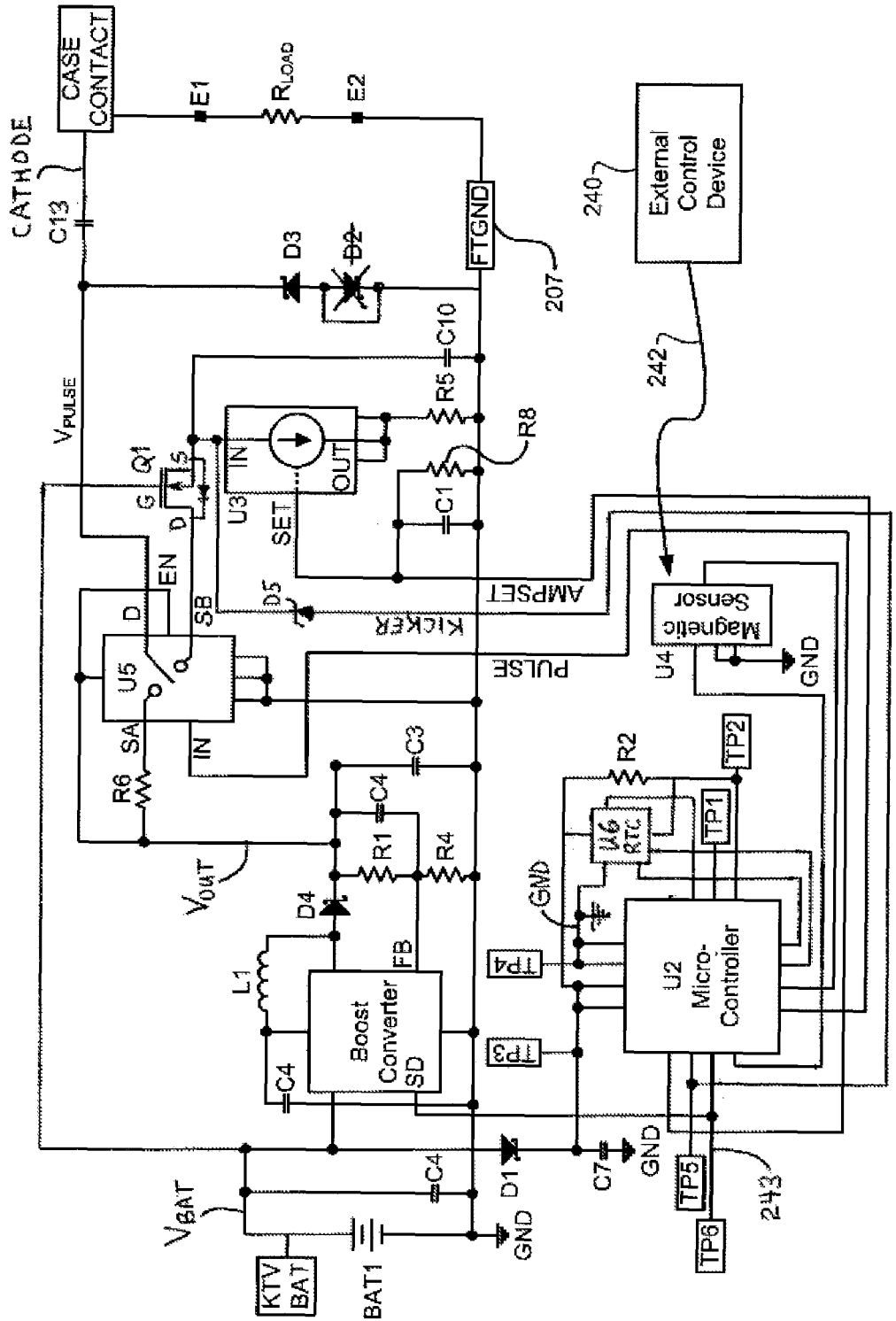
FIG. 15C shows another preferred schematic configuration for an IEAD similar to that shown in FIGS. 13A, 14 and 14A, which includes all the additional enhancements included in the circuit of FIG. 14A, and further includes a real time clock (RTC) module to better facilitate and manage chronotherapeutic applications of the stimulation regimen.

A schematic diagram of an IEAD design that uses such an RTC Module to replace the crystal time base presently used with the micro-controller U2 is shown in FIG. 15C. In most respects, the circuit shown in FIG. 15C is the same as the circuit shown in FIG. 14A. The one key difference between the IEAD circuit of FIG. 15A and the IEAD circuit of FIG. 14A, is the insertion of a RTC module U6. As seen in FIG. 15C, the RTC module U6 is connected to the micro-controller circuit U2 and replaces the previously-used external crystal oscillator. The RTC module U6 is able to be set to wake up the micro-controller circuit U2 when needed, and/or put the micro-controller U2 in a shut-down (sleep) state when not needed. Advantageously, the shut down mode is even a lower power state than is achieved with the sleep state controlled by the previously-used external crystal oscillator.

From the above description, it is seen that an implantable IEAD 100 is provided that uses a digital control signal to duty-cycle limit the instantaneous current drawn from the battery by a boost converter. Three different exemplary functional configurations (FIGS. 10, 11 and 12) are taught for achieving this desired result, and four exemplary circuit designs, or implementations, have been presented that may be used to realize the desired configurations (FIGS. 13A, 14, 14A and 15C). One implementation (FIG. 15C), in addition to including all the enhancements added to the base implementation circuit of FIG. 13A (to address, e.g., problems of slow starts, delays, and needed circuit isolation, and to add improvements such as better switching, reverse trapezoidal stimulation wave shapes and EMI protection), teaches the use of a real time clock module to provide a crystal time base to facilitate the use of chronotherapeutics. One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

Use and Operation

With the implantable electroacupuncture device (IEAD) 100 in hand, the IEAD 100 may be used most effectively to treat a specified disease or medical condition of the patent by first pre-setting stimulation parameters that the device will use during a stimulation session. FIGS. 15A and 15B show timing waveform diagrams illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01, but may, in some instances, be as much as 0.03. The duration of a stimulation session is dictated or defined by the time period T3. The amplitude of the stimulation pulses is defined by the amplitude A1. This amplitude may be expressed in either voltage or current.

FIG. 15B illustrates the manner in which the stimulation sessions are administered in accordance with a specified stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4(min). Then, as time goes on, the value of T4 may be gradually increased until a desired value of T4, T4(final), is reached.

By way of example, if T4(min) is 1 day, and T4(final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table that defines session durations and intervals whereby the automatic session interval can be shorter for the first week or so. For example, T3 is 30 minutes, the first 30 minute session could be delivered after 1 day. The second 30 minute session could be delivered after 2 days. The third 30 minute session could be delivered after 4 days. Finally, the $4^{th}$ 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. If the first session is aborted by a magnet application, the device reverts to a Shelf Mode. In this way, the first session is always a triggered session that occurs in the clinician setting.

Finally, the amplitude and place in the session table are saved in non-volatile memory when they change. This avoids a resetting of the therapy schedule and need to reprogram the amplitude in the event of a device reset.

By way of example, one preferred set of parameters that could be used to define a stimulation regimen is as follows:
T1=0.5 milliseconds
T2=500 milliseconds
T3=30 minutes
T4=7 days (10,080 minutes)
A1=15 volts (across 1 KΩ), or 15 milliAmps (mA)

An example of typical ranges for each parameter, for treating a particular condition or disease, is as follows:
T1=0.1 to 2.0 milliseconds (ms)
T2=67 to 1000 ms (15 Hz to 1 Hz)
T3=20 to 60 minutes
T4=1,440 to 10,080 minutes (1 day to 1 week)
A1=1 to 15 mA It is to be emphasized that the values shown above for the stimulation regimen and ranges of stimulation parameters for use within the stimulation regimen are only exemplary. Other stimulation regimens that could be used, and the ranges of values that could be used for each of these parameters, are as defined in the claims.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant at the desired stimulation site (e.g., acupoint), but it also limits the frequency and duration of stimulation sessions.

Limiting the frequency and duration of the stimulation sessions is a key aspect of Applicant's invention because it recognizes that some treatments are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce a sustained therapeutic effect. Thus, Applicant has based its treatment regimen on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit U2, the IEAD 100 needs to be implanted. Implantation is usually a simple procedure, and is described above in connection, e.g., with the description of FIGS. 1A and 1B.

Figure 16:
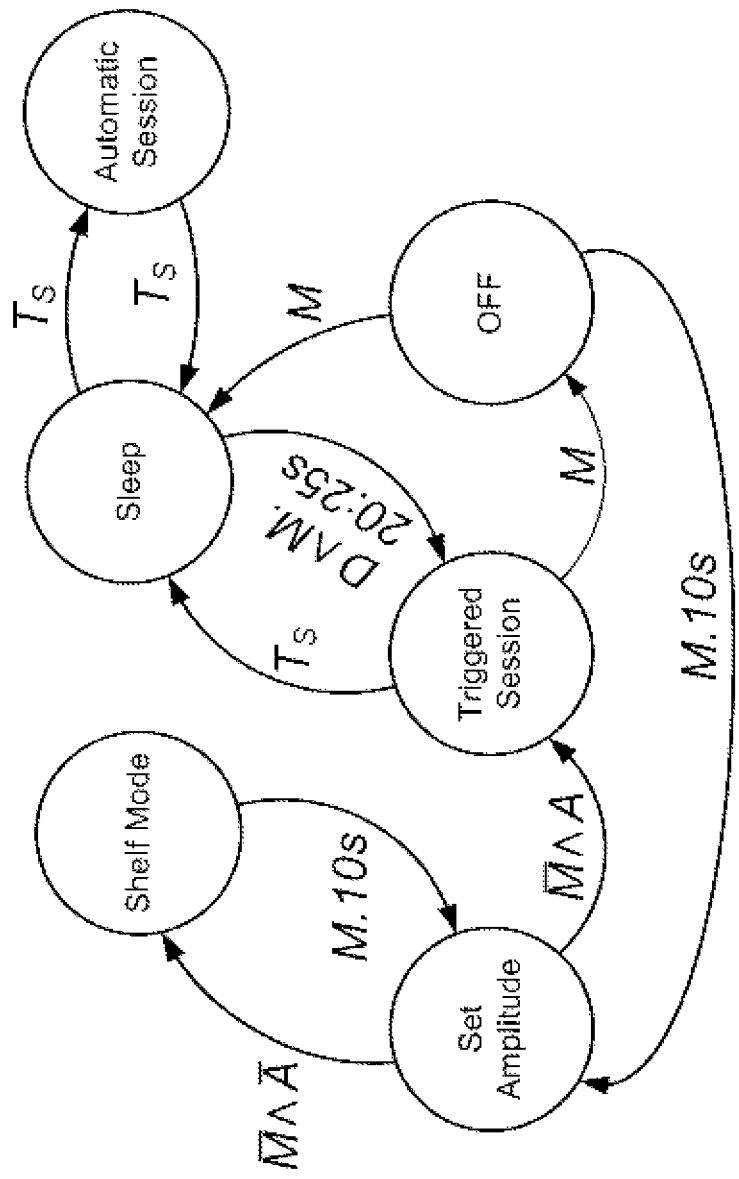
FIG. 16 shows a state diagram that depicts the various states the IEAD circuitry may assume as controlled by an external magnet.

After implantation, the IEAD must be turned ON, and otherwise controlled, so that the desired stimulation regimen or stimulation paradigm may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents an operating "state" of the micro-controller U2 (FIGS. 13A, 14, 14A of 15C). As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10 s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M}\Lambda A$), the device continues into the "Triggered Session" so the patient receives the initial therapy. If the magnet is removed during "Set Amplitude" while the amplitude is zero ($\overline{M}\Lambda\overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10 s) while in the "OFF" state, the "Set Amplitude" state is entered with the stimulation level starting from zero amplitude as described.

If the magnet is removed (M) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20:25 s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14A) for controlling the states of the IEAD as shown in FIG. 16 is found in Appendix C, attached hereto, and incorporated by reference herein.

In the preceding description, various exemplary embodiments have been described with reference to the accompanying drawings and appendices. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teachings. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. An Implantable ElectroAcupuncture Device (IEAD) for treating a specified medical condition of a patient through application of electroacupuncture (EA) stimulation pulses adapted to be applied substantially at or near a specified target tissue location, comprising:
  a small IEAD housing having an electrode configuration thereon that includes at least two electrodes/arrays, the longest linear dimension of the small IEAD housing being no greater than about 25 mm, and the shortest linear dimension, measured orthogonal to the longest linear dimension, is no greater than about 2.5 mm, wherein at least one of said at least two electrodes/arrays comprises a central electrode/array located substantially in the center of a first surface of the IEAD housing, and wherein at least another of said at least two electrodes/arrays comprises a circumferential electrode/array located substantially around and at least 5 mm distant from the center of the central electrode/array, wherein the first surface (106) of the IEAD housing when implanted is adapted to face inwardly into the patient's tissue at or near the specified target tissue location;
  pulse generation circuitry located within the IEAD housing and electrically coupled to the at least two electrodes/arrays, wherein said pulse generation circuitry is adapted to deliver stimulation pulses to the patient's body tissue at or near the target tissue location in accordance with a specified stimulation regimen, said stimulation regimen defining the duration (T3) and rate (1/T4) at which a stimulation session is applied to the patient, said stimulation regimen requiring that the stimulation session have a duration of T3 minutes and a rate of occurrence of once every T4 minutes, wherein the ratio of T3/T4 is no greater than 0.05, and wherein during each stimulation session EA stimulation pulses having one or more specified widths (T1) and amplitudes (A1) are generated at one or more specified rates (1/T2);
  a primary battery contained within the IEAD housing and electrically coupled to the pulse generation circuitry that provides operating power for the pulse generation circuitry, said primary battery having a nominal output voltage of 3 volts, and an internal impedance greater than 5 ohms; and
  a sensor contained within the IEAD housing responsive to operating commands wirelessly communicated to the IEAD from a non-implanted location, said operating commands allowing limited external control of the IEAD.

2. The IEAD of claim 1 wherein the circumferential electrode/array comprises an anode electrode/array and the central electrode/array comprises a cathode electrode/array.

3. The IEAD of claim 1 wherein the small IEAD housing is coin-shaped having a diameter no greater than about 25 mm and a thickness of no greater than about 2.5 mm.

4. The IEAD of claim 3 wherein the specified medical condition comprises at least one of (1) hypertension, (2) cardiovascular disease, (3) depression, (4) bipolar disorder, (5) Anxiety, (6) obesity, (7) dyslipidemia, (8) Parkinson's disease, (9) Essential tremor, or (10) erectile dysfunction.

5. The IEAD of claim 4 wherein the specified target tissue location comprises at least one acupoint selected from the group of acupoints comprising: BL14, BL23, BL52, EXHN1, EXHN3, GB34, GV4, GV20, HT5, HT7, KI6, L14, LI11, LR3, LR8, LU2, LU7, PC5, PC6, PC7, SP4, SP6, SP9, ST36, ST37, and ST40.

6. The IEAD of claim 1 wherein the pulse generation circuitry includes:
a boost converter circuit that boosts the nominal voltage of the primary battery to an output voltage $V_{OUT}$ that is at least three times the nominal battery voltage;
means for selectively turning the boost converter circuit OFF and ON to limit the amount of current that may be drawn from the primary battery; and
an output circuit powered by $V_{OUT}$ that generates the stimulation pulses as defined by the specified stimulation regimen.

7. The IEAD of claim 6 wherein the stimulation pulses generated by the pulse generation circuit and delivered through the at least two electrodes/arrays into a load at the target tissue location comprise current pulses having a current amplitude of no less than about 1 milliampere (mA) and no greater than about 25 mA.

8. The IEAD of claim 7 wherein the primary battery has sufficient capacity to power the pulse generation circuitry in accordance with the specified stimulation regimen for a minimum of 2 years.

9. The IEAD of claim 6 wherein the means for selectively turning the boost converter circuit OFF and ON comprises a control circuit configured to generate a digital signal that modulates the boost converter circuit between an OFF state and an ON state, with the ON state comprising no more than about 2% of the time that the IEAD is operating.

10. The IEAD of claim 6 wherein the means for selectively turning the boost converter circuit OFF and ON comprises a boost converter circuit having a shut down feature which automatically places the boost converter circuit in an OFF state whenever the battery voltage falls below a set minimum value, wherein the set minimum value of the battery below which the boost converter is placed in an OFF state comprises a voltage that is sufficiently high to continue to power other digital processing circuits within the pulse generation circuitry even when the boost converter is turned OFF.

11. The IEAD of claim 10 wherein the pulse generation circuitry further includes circuitry configured to create a reverse trapezoidal stimulation pulse waveshape for the stimulation pulses.

12. The IEAD of claim 11 wherein the pulse generation circuitry further includes means for reducing leading edge transient signals that may be present in the stimulation pulses generated by the pulse generation circuitry.

13. The IEAD of claim 12 wherein the output circuit of the pulse generation circuitry includes a programmable current source, and wherein the means for reducing leading edge transient signals comprises connecting a cascode circuit at the input of the programmable current source.

14. The IEAD of claim 13 wherein the pulse generation circuitry further includes means for kick starting the programmable current source when low amplitude stimulation pulses are generated, wherein such kick starting eliminates or reduces undesired delays in the leading edge of the stimulation pulses generated by the pulse generation circuitry.

15. The IEAD of claim 11 wherein the specified medical condition comprises hypertension and wherein the specified target tissue location comprises at least one of the acupoints PC5, PC6, ST36 or ST37.

16. The IEAD of claim 11 wherein the specified medical condition comprises at least one of depression, bipolar disorder and Anxiety, and wherein the specified target tissue location comprises at least one of the acupoints GV20 or EXHN3.

17. The IEAD of claim 11 wherein the specified medical condition comprises cardiovascular disease and wherein the specified target tissue location comprises at least one of the acupoints: BL14, EXHN1, HT5, HT7, LI11, LU2, LU7, PC6, or ST36.

18. The IEAD of claim 11 wherein the specified medical condition comprises dyslipidemia or obesity and wherein the specified target tissue location comprises at least one of the acupoints: KI6, LR8, SP4, SP6, SP9, ST36, ST37 or ST40.

19. The IEAD of claim 11 wherein the specified medical condition comprises Parkinson's disease or Essential tremor and wherein the specified target tissue location comprises at least one of the acupoints GB34 or GV20.

20. The IEAD of claim 11 wherein the specified medical condition comprises erectile dysfunction and wherein the specified target tissue location comprises at least one of the acupoints GV4, BL23 or BL52.

* * * * *